(12) United States Patent
Smith

(10) Patent No.: US 12,110,223 B2
(45) Date of Patent: Oct. 8, 2024

(54) APPARATUS FOR RUPTURING A SEALED, FRANGIBLE CONTAINER

(71) Applicant: Zachary Bradford Smith, Phoenix, AZ (US)

(72) Inventor: Zachary Bradford Smith, Phoenix, AZ (US)

( * ) Notice: Subject to any disclaimer, the term of this patent is extended or adjusted under 35 U.S.C. 154(b) by 788 days.

(21) Appl. No.: 17/175,108

(22) Filed: Feb. 12, 2021

(65) Prior Publication Data

US 2021/0246009 A1    Aug. 12, 2021

Related U.S. Application Data

(60) Provisional application No. 62/975,355, filed on Feb. 12, 2020.

(51) Int. Cl.
  *B67B 7/92*   (2006.01)
  *A61J 1/06*   (2006.01)
  *A61M 35/00*  (2006.01)

(52) U.S. Cl.
  CPC .............. *B67B 7/92* (2013.01); *A61J 1/065* (2013.01); *A61M 35/006* (2013.01)

(58) Field of Classification Search
  CPC ........... A61J 1/1406; A61J 1/065; B67B 7/92; A61M 35/003; A61M 35/00; A61M 35/006; A45D 2200/1045

USPC .................................. 215/48; 206/222, 219
  See application file for complete search history.

(56) References Cited

U.S. PATENT DOCUMENTS

| | | | |
|---|---|---|---|
| 2,700,972 | A | 2/1955 | Haden |
| 4,304,869 | A | 12/1981 | Dyke |
| 5,405,580 | A | 4/1995 | Palmer |
| 7,306,390 | B2 | 12/2007 | Quintero et al. |
| 7,516,872 | B2 | 4/2009 | Boone et al. |
| 9,775,977 | B2 | 10/2017 | Dombrowski et al. |
| 2005/0111900 | A1 | 5/2005 | Fazzolari et al. |
| 2021/0220868 | A1* | 7/2021 | Hiemer ............... B05C 17/0133 |

FOREIGN PATENT DOCUMENTS

WO    WO2019219130    11/2019

* cited by examiner

*Primary Examiner* — Anthony D Stashick
*Assistant Examiner* — Raven Collins
(74) *Attorney, Agent, or Firm* — Woodard, Emhardt, Henry, Reeves & Wagner, LLP

(57) ABSTRACT

An opening structure including opening methods and elements to fracture a glass ampoule in a safe, secure, and friendlier manner at a specific point on the ampoule, which allows the ampoule to retain in place its substantial structure, allowing less glass fragments from the ampoule's breakage to obstruct the smooth, consistent, and speedy flow of the ampoule's substance to the opening structure's dispenser/applicator.

14 Claims, 28 Drawing Sheets

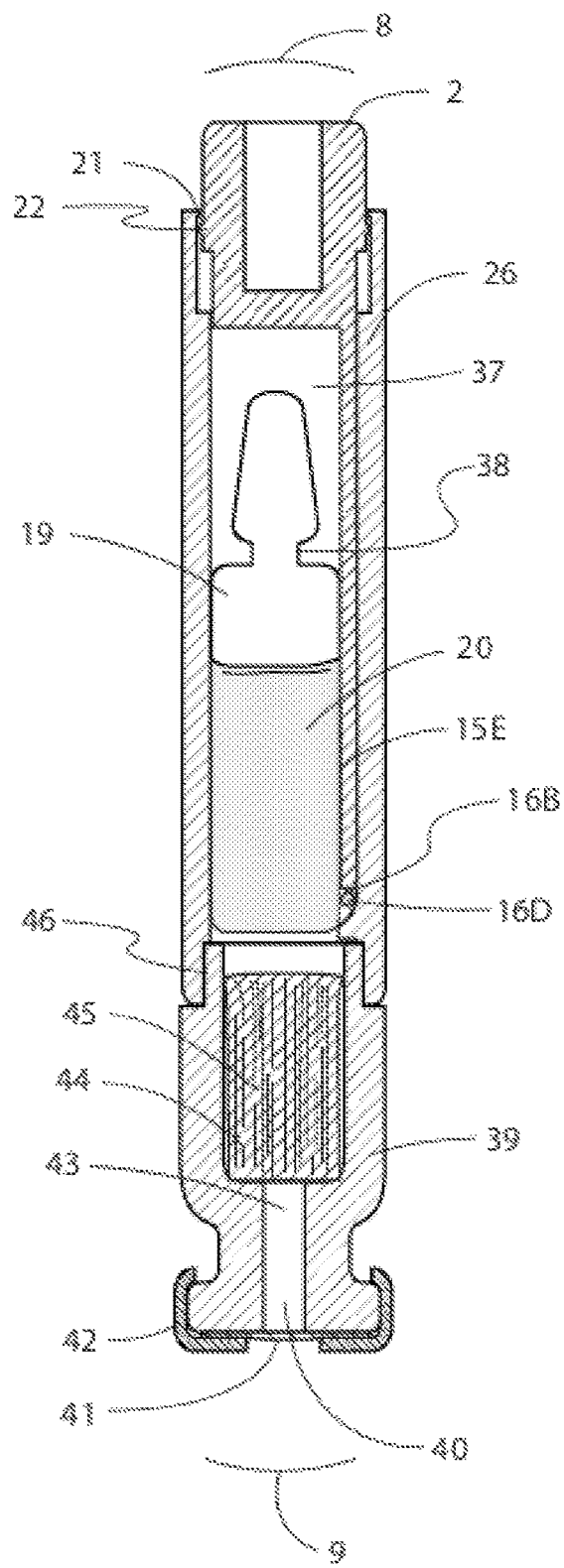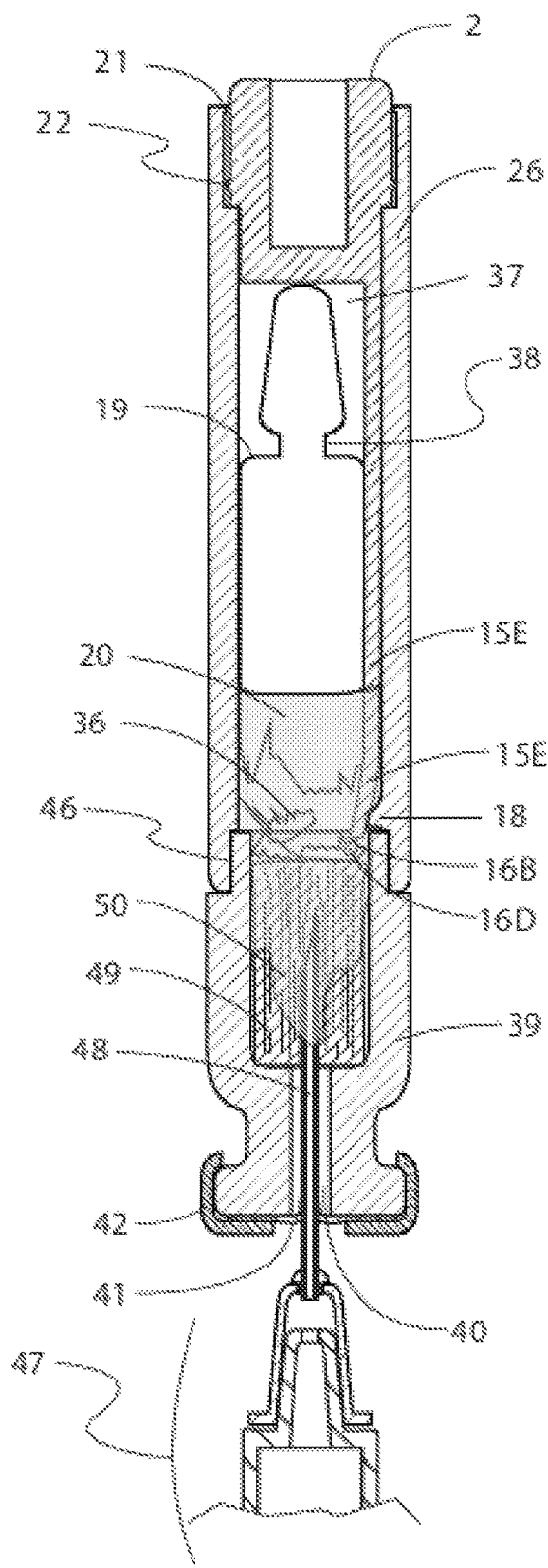
FIG. 19
FIG. 20

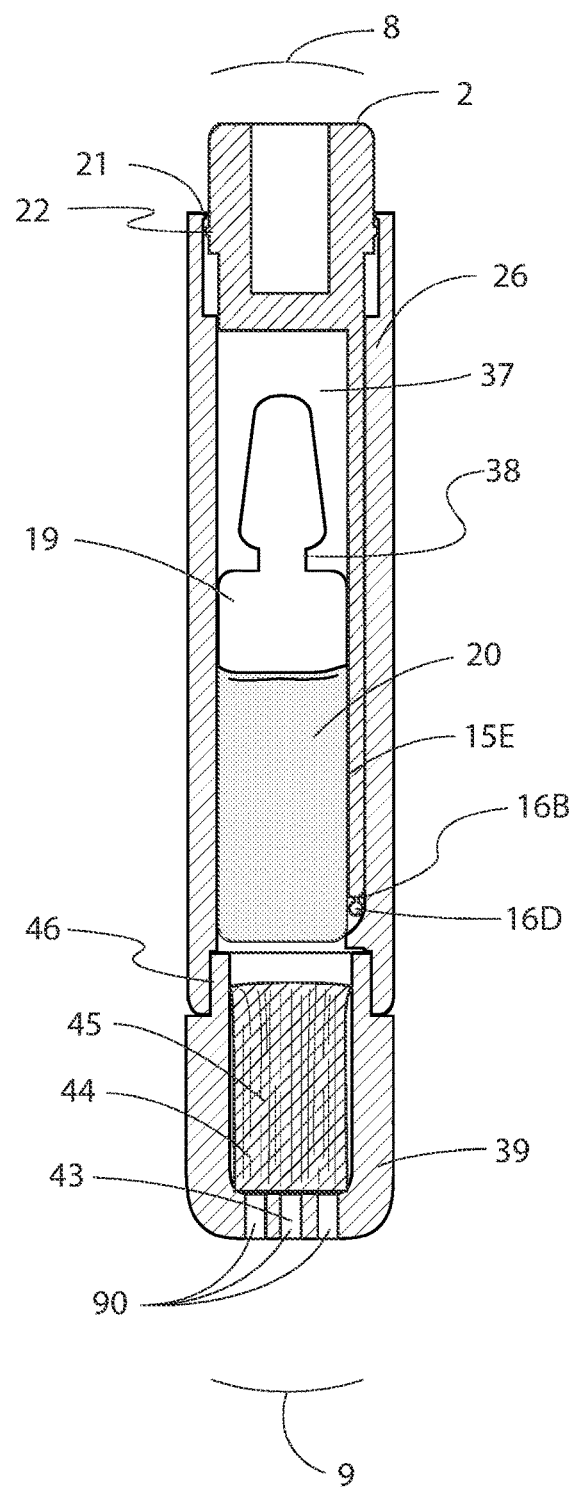
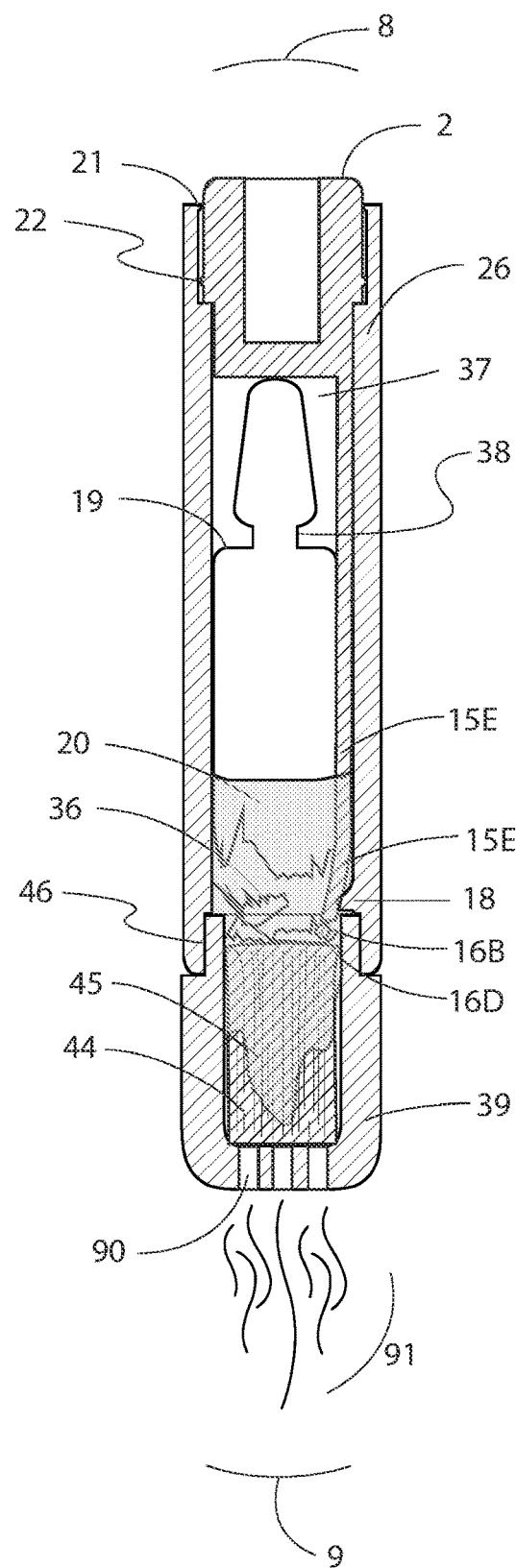
FIG. 26A
FIG. 26B

APPARATUS FOR RUPTURING A SEALED, FRANGIBLE CONTAINER

CROSS-REFERENCE TO RELATED APPLICATION

This application claims the benefit of U.S. Provisional Application No. 62/975,355 filed Feb. 12, 2020, which is hereby incorporated by reference.

BACKGROUND OF THE INVENTION

Field of Invention

Embodiments of the present invention generally relate to frangible hermetically sealed ampoules made of glass. Other materials, such as a pierceable plastic material, or a pierceable metal material, such as aluminum, may be used for the frangible ampoule. Other embodiments include ampoule opening structures; ampoule opening methods; and, dispensers/applicators to dispense and/or apply the substance contained within the ampoules.

Description of Related Art

Prior art references relating to the opening methods; opening structures; and, dispensers/applicators for frangible ampoules, particularly glass ampoules are known, and are described in earlier patents. Those patents describe a wide variety of structures, and certain ampoule opening methods, including the dispensers/applicators associated with the structures. Many of the structures and their operation are complex; others have parts that require tedious costly assembly processes; and, many include delicate or fragile construction, making them difficult to make or use, or both. Some of the prior art patents further disclose ampoule-opening methods that require the user to hand-crush a sleeved ampoule, which can present a wincing apprehensive experience for the user, as well as safety concerns.

While certain of these structures may have purported advantages, there is a need to have a user-friendlier, simpler, safer, and more effective ampoule opening structure and opening method that consistently and accurately breaks an ampoule at its best structural location providing the least amount of glass fragments occurring from the ampoule's breakage, providing an optimum flow rate of the flow-able substance from the ampoule to the dispenser/applicator.

The present invention overcomes one or more of the shortcomings found in the prior art, represented, in part, by the prior art listed herein. Pub. No. U.S. 2005/0111900A1 discloses a fluid dispenser having a sleeved glass ampoule, which is crushed upon the user pressing their thumb and forefinger at designated positions indicated on the ampoule's sleeve. U.S. Pat. No. 9,775,977 discloses a device to crush a glass ampoule located within a housing, upon a lever being depressed by the user. U.S. Pat. No. 2,700,972 discloses a unique apparatus to fracture (not crush) an ampoule held within a container by applying a wedging moment against the glass ampoule's exterior wall. U.S. Pat. Nos. 7,516,872; 7,306,390; 4,304,869; 5,405,580; and, Pat. Pub. No. WO2019219130 disclose various pen-like devices that cleverly fracture or pierce ampoules.

SUMMARY OF THE INVENTION

The present invention's preferred embodiments overcome the disadvantages and/or shortcomings of the conventional ampoule opening methods and opening structures by having a two-part opening structure and a one-step opening method. The two-part opening structure, has a first-part consisting of a substantially rigid housing that supports at least one ampoule, and a second-part consisting of push button having a telescopic push-rod with a tethered spherical ball. Both parts can be simply made from a plastic polymer and/or a combination of polymers such as polyethylene and Delrin®, and are easily manufactured through injection molding processes utilizing clear-cut straightforward tooling.

In one of the preferred embodiments, the housing has clearance between the ampoule's outside diameter and its internal diameter to provide a pathway for the push-rod to travel linearly. In yet another embodiment the housing has an internal recessed guide channel that helps support the linear movement of the push-rod. As will be been seen later within the Brief and Detailed Descriptions, these embodiments provide flexibility to adapt to the various sizes, structural shapes, and contents of ampoules currently in use.

Further embodiments include a push button having an external seal at its distal end that coincides with the internal diameter of the housing, and the housing having an internal seal that coincides with the outside diameter of the push button.

A brief general explanation of the two-part opening structure and the one-step opening method will now be provided. It should be noted that the example and the accompanying details that are provided, are strictly for the purposes of understanding the overall operation of the opening structure and opening method, and should not limit in any way the scope of the invention's embodiments.

The ampoule is snuggly contained within the opening structure. The exampled ampoule has an approximate length of 1.490 inches with an outside diameter of approximately 0.0277 inches and a wall thickness of 0.010 inches with a radius domed end having a radius of 0.138 inches. (See FIG. 25)

In operation, the push button, located on the proximal end of the opening structure, is pushed downward 0.250 of an inch with approximately four (4) pounds-force which meets the Department of Defense Design Criteria Standards: MIL-STD 1472F. The push-rod, having a length from the top of the push button to the center of the spherical ball of approximately 2.072 inches, moves with a snap-action instantaneous linearly downward motion from the housing's proximal end the same 0.250 inches. The push-rod's tethered ball having a tether with a diameter of approximately 0.040 inches and a tether length of approximately 0.014 inches; and, a ball diameter of approximately 0.0625 moves onto a round shaped kick-in at the housing's distal end having a radius of approximately 0.500.

When the push-rod has extended the 0.250 inches the spherical ball accelerates and slightly deflects from its linear axis with a vector of approximately 18.6 pounds-force and with an inward thrust travel of 0.080 inches into the sidewall of the ampoule, fracturing the ampoule at a preferred specific point having a distance of approximately 0.312 inches from the ampoule's distal end and 1.178 inches from the ampoule's proximal end.

Fracturing the ampoule with an instantaneous given force at a specific point on the ampoule will leave approximately eighty percent (80%) of the ampoule's upper proximal structure intact, resulting in less glass fragments collecting at the distal end of the opening structure providing for better consistent flow of the ampoule's flow-able substance into the opening structure's press pad area and then out to the opening structure's dispenser/applicator tip.

Other embodiments will be described which show opening structures that can accept more than one ampoule wherein multiple ampoules can be made of different materials (e.g. glass, plastic, metal foil, etc.); have different sizes in diameters and lengths; and can be instantaneously pierced, broken and/or fractured with a staggered different timing—all within the same action of the push stroke by the push button within the opening structure disclosing additional opening methods that reflect the simplicity and versatility of the invention.

BRIEF DESCRIPTION OF THE DRAWINGS

FIG. 19 and FIG. 20 present cross-sectional side and front views showing a necked type ampoule for discharging (extracting) the ampoule's contents into a syringe type device.

FIGS. 26A and 26B show cross-sectional views of the vapor emitter dispenser tip having a multi-ported casing that allows exiting of vapors, but not liquid.

DETAILED DESCRIPTION OF THE PREFERRED EMBODIMENT

In order to properly explain the detail relative to the opening structure and opening methods, it will be best to first briefly describe the embodiments of an assembled single glass ampoule unit.

Figure 1:
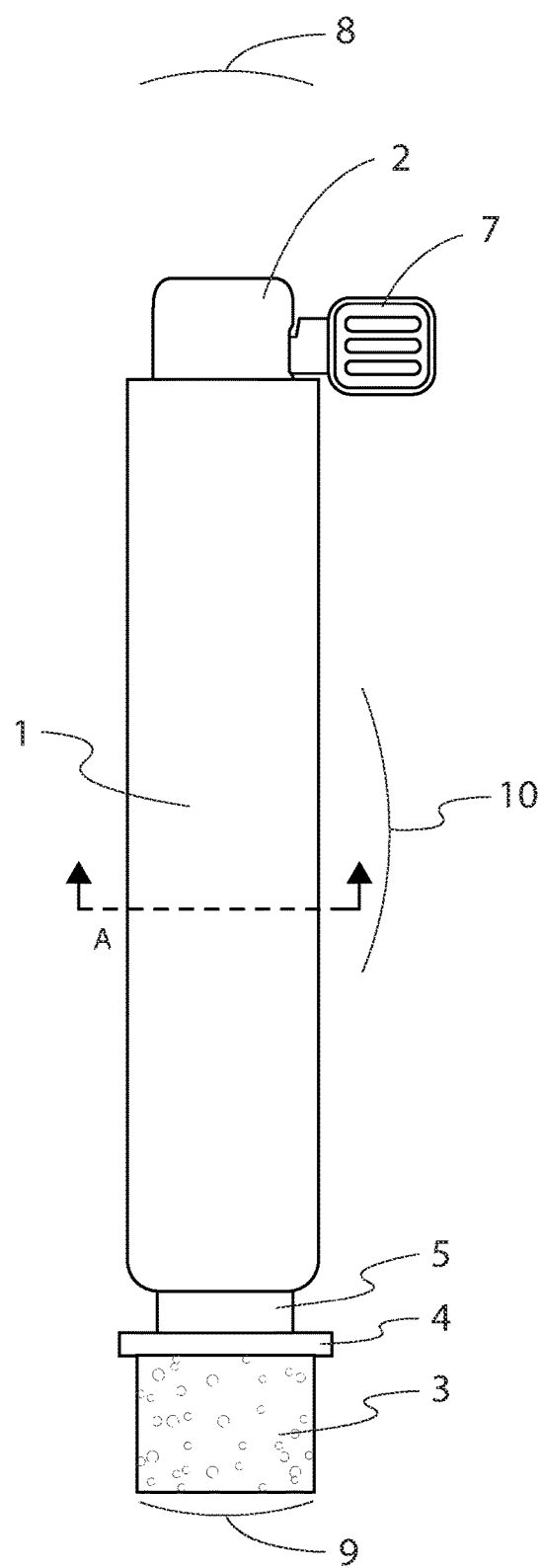
FIG. 1 is a side view of the opening structure showing the proximal and distal ends for a single ampoule embodiment.
Figure 2:
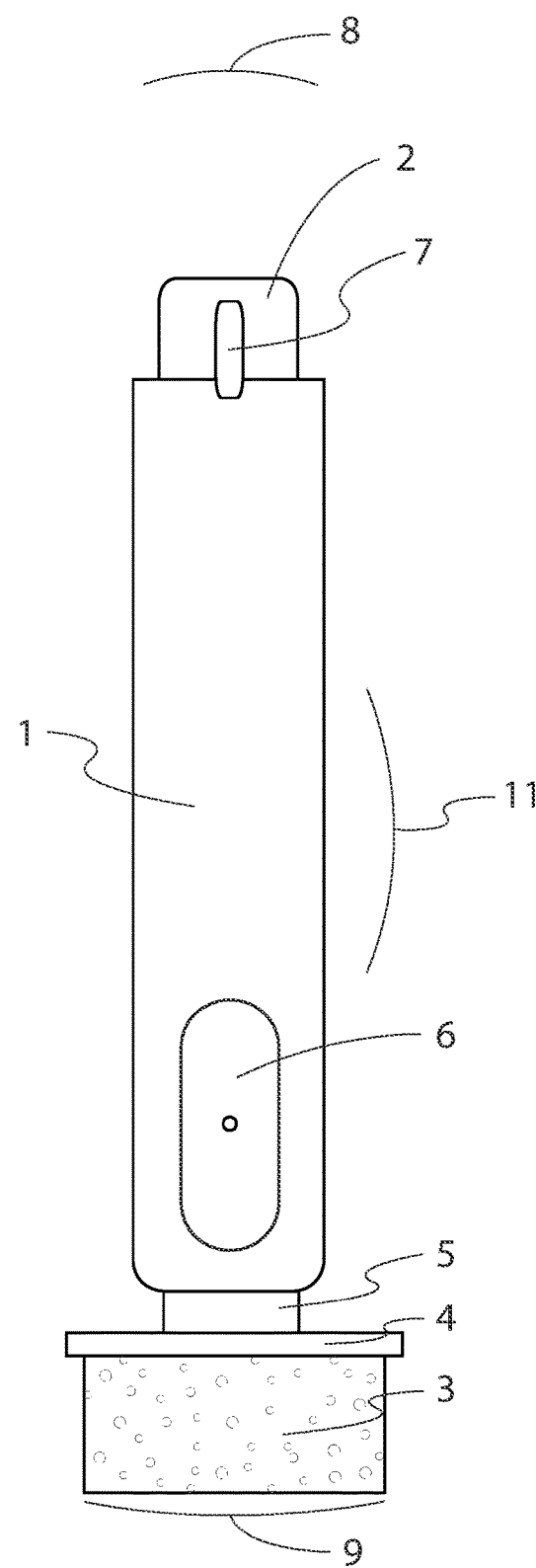
FIG. 2 is a front view of the opening structure showing the proximal and distal ends for a single ampoule embodiment.
Figure 21:
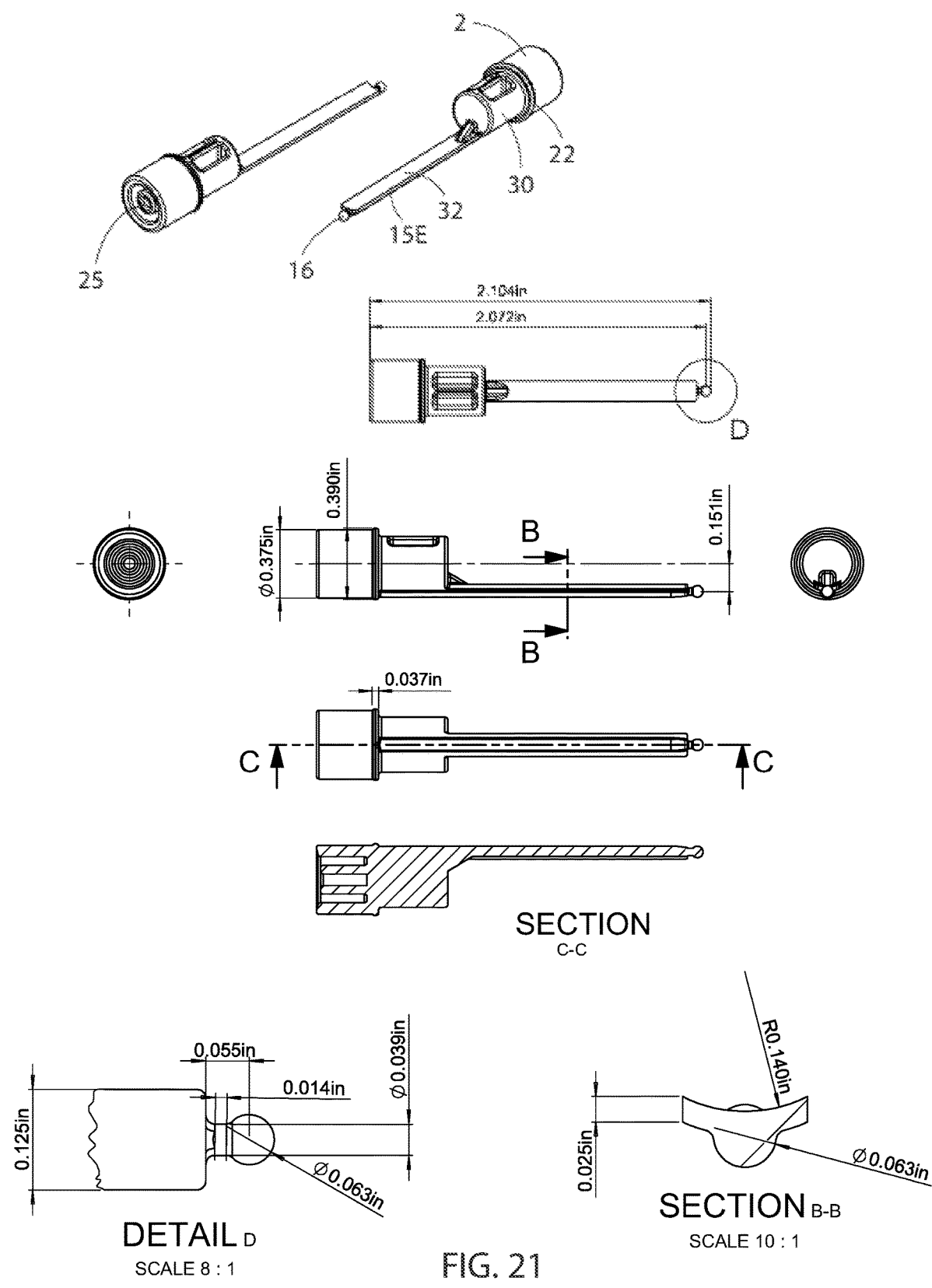
FIG. 21 shows dimensional and orthographic views of the push button and push-rod tethered ball assemblies that operate free of a housing's internal channel guide.
Figure 25A:
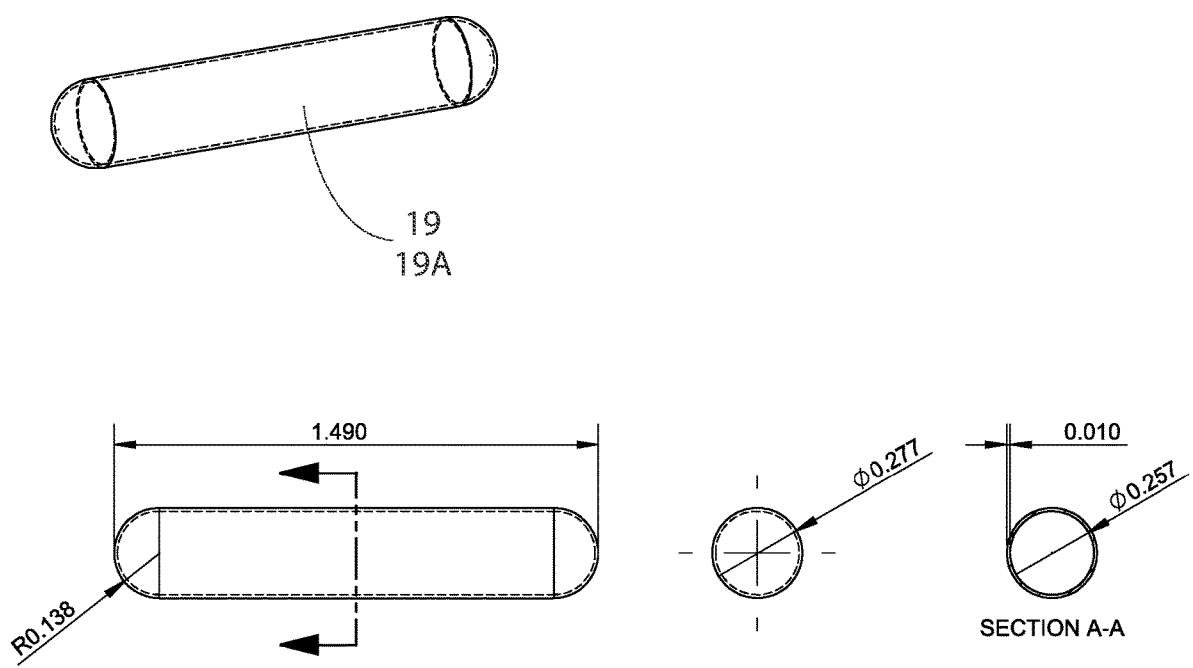
FIG. 25A presents a dimensional drawing of representative glass ampoule.
Figure 27:
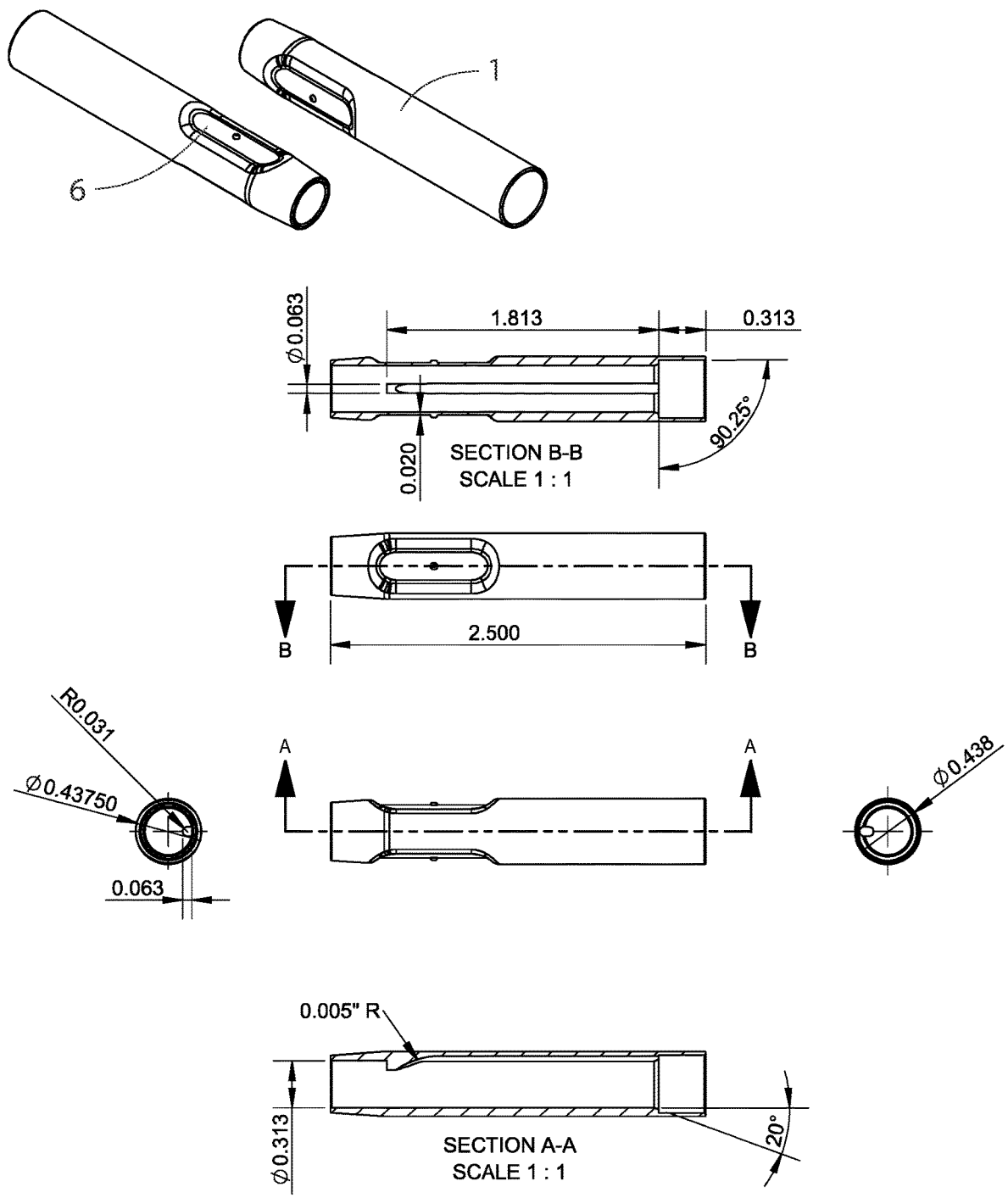
FIG. 27 presents a dimensional drawing of the opening structure's housing.
Figure 28:
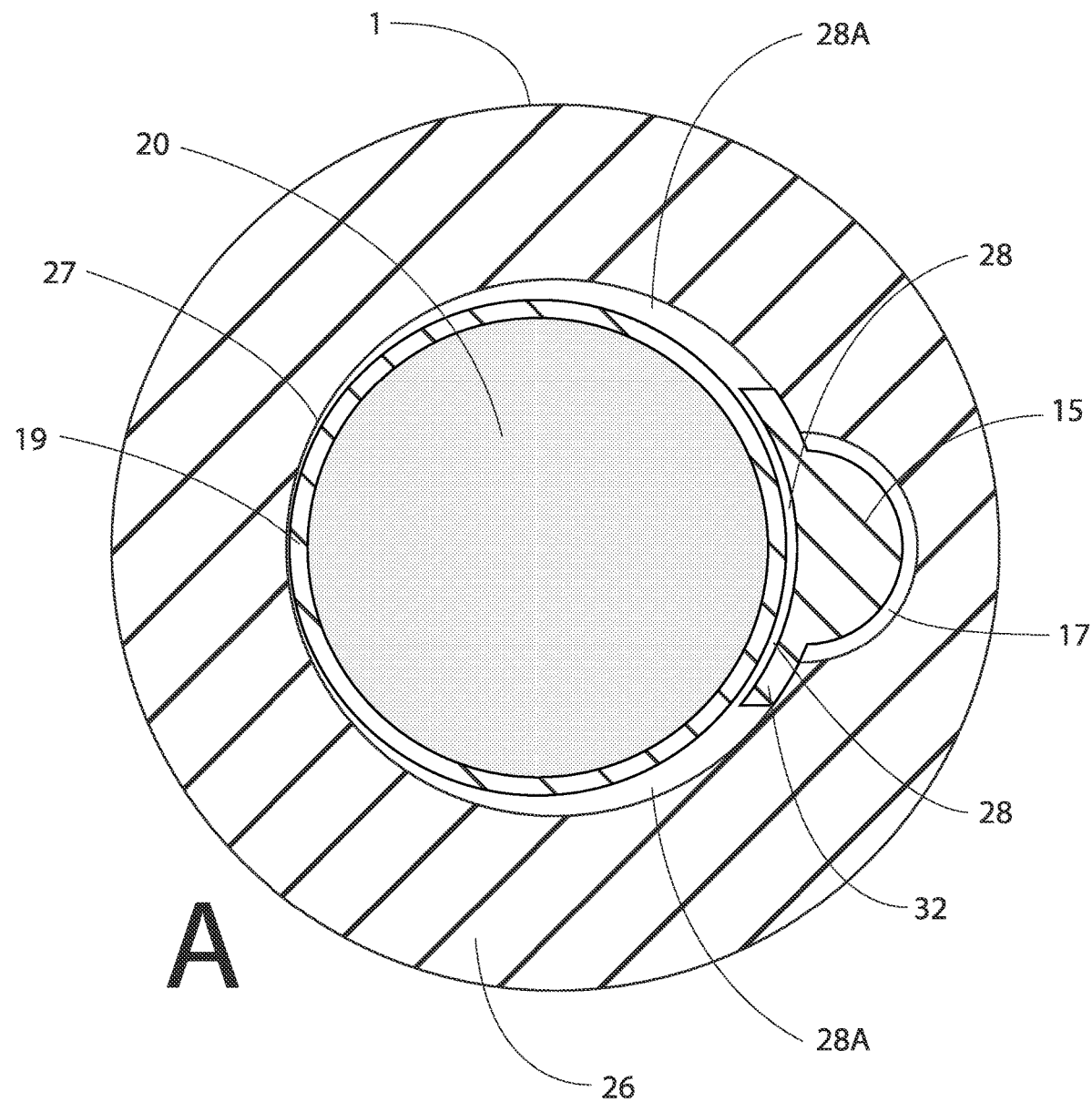
FIGS. 28 and 29 represent section drawings A and AA of the opening structure's housing and opening methods and elements.
Figure 29:
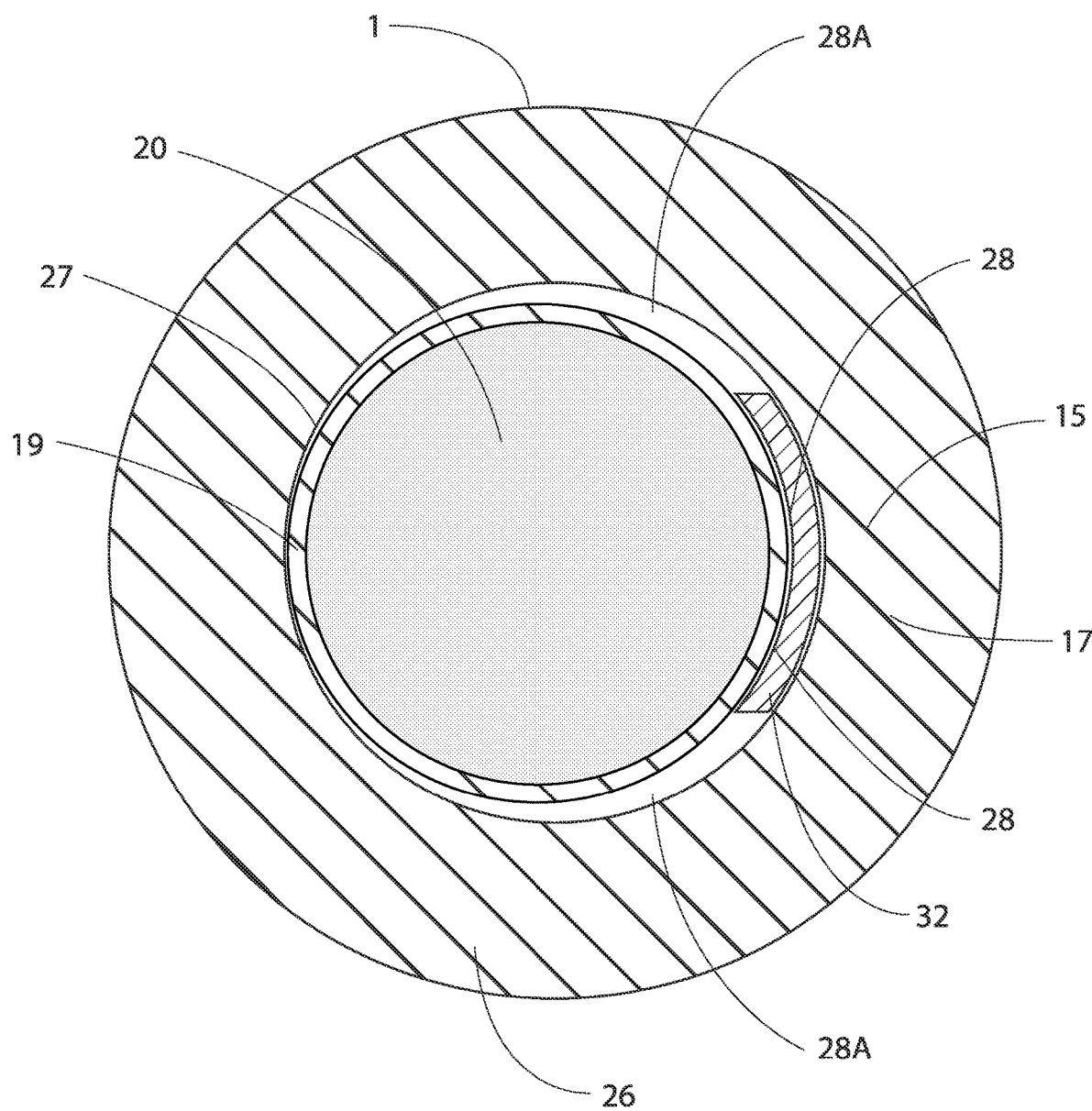
Figure 30:
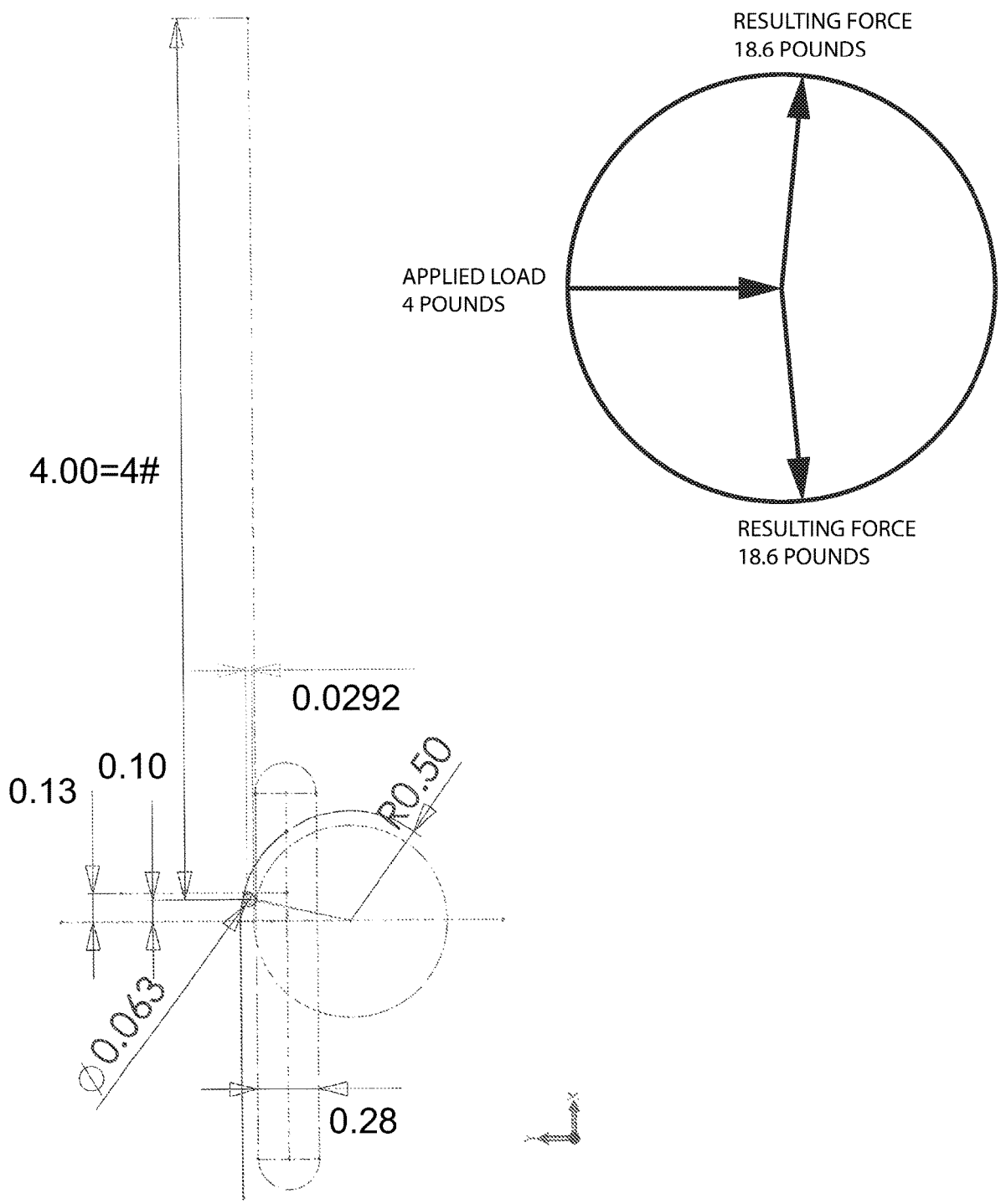
FIGS. 30, 31, 32, 33, and 34 present data relative to the vector forces involved with the opening structure and the opening methods.
Figure 31:
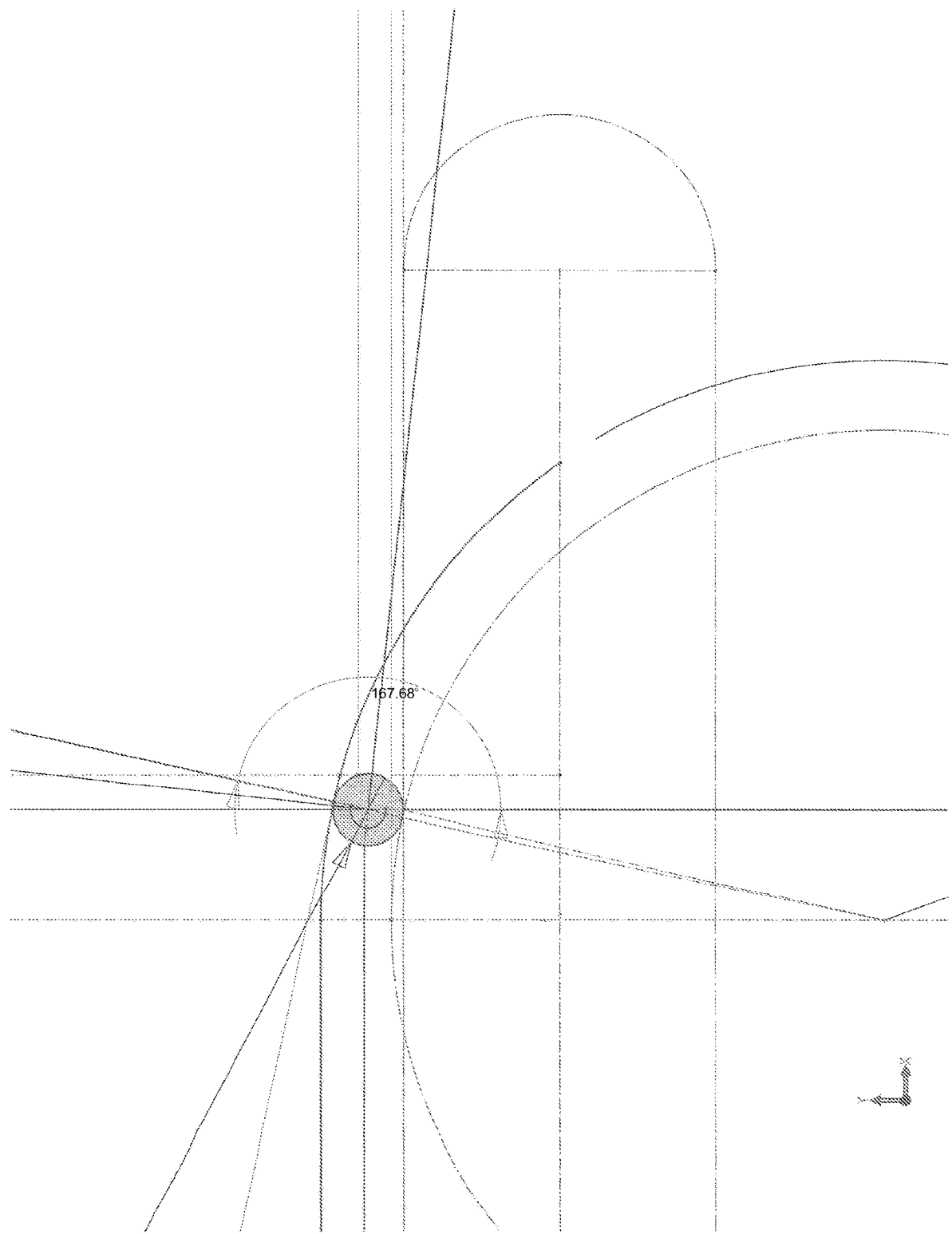
Figure 32:
Figure 32:
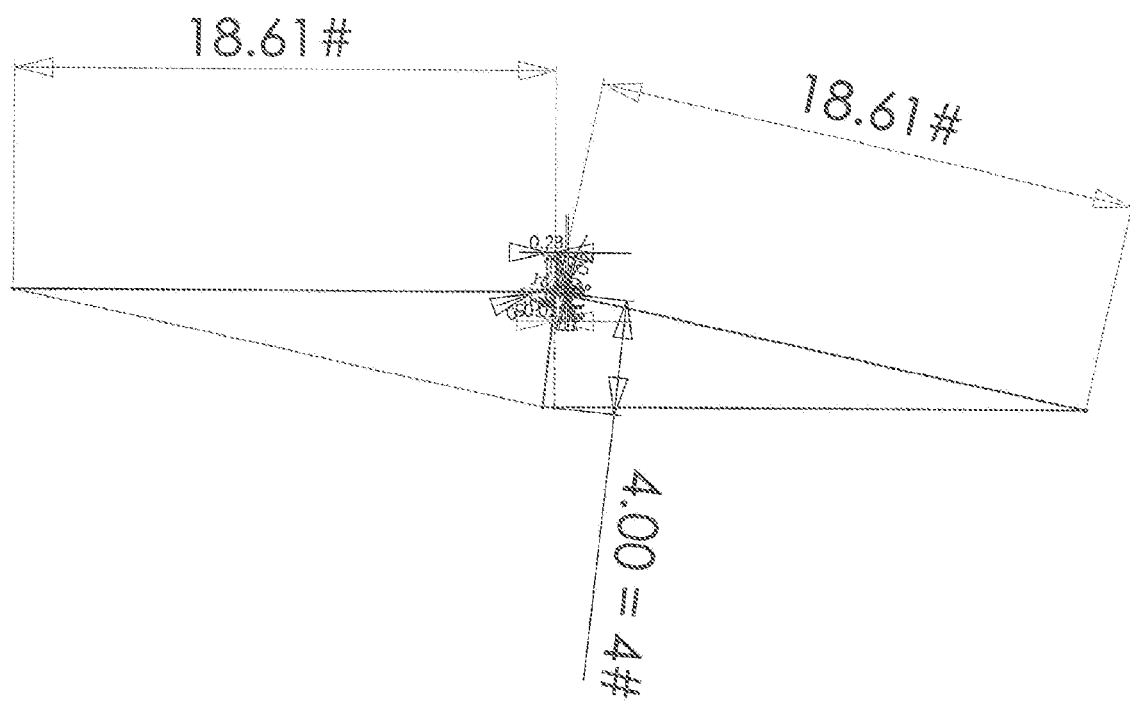
Figure 33:
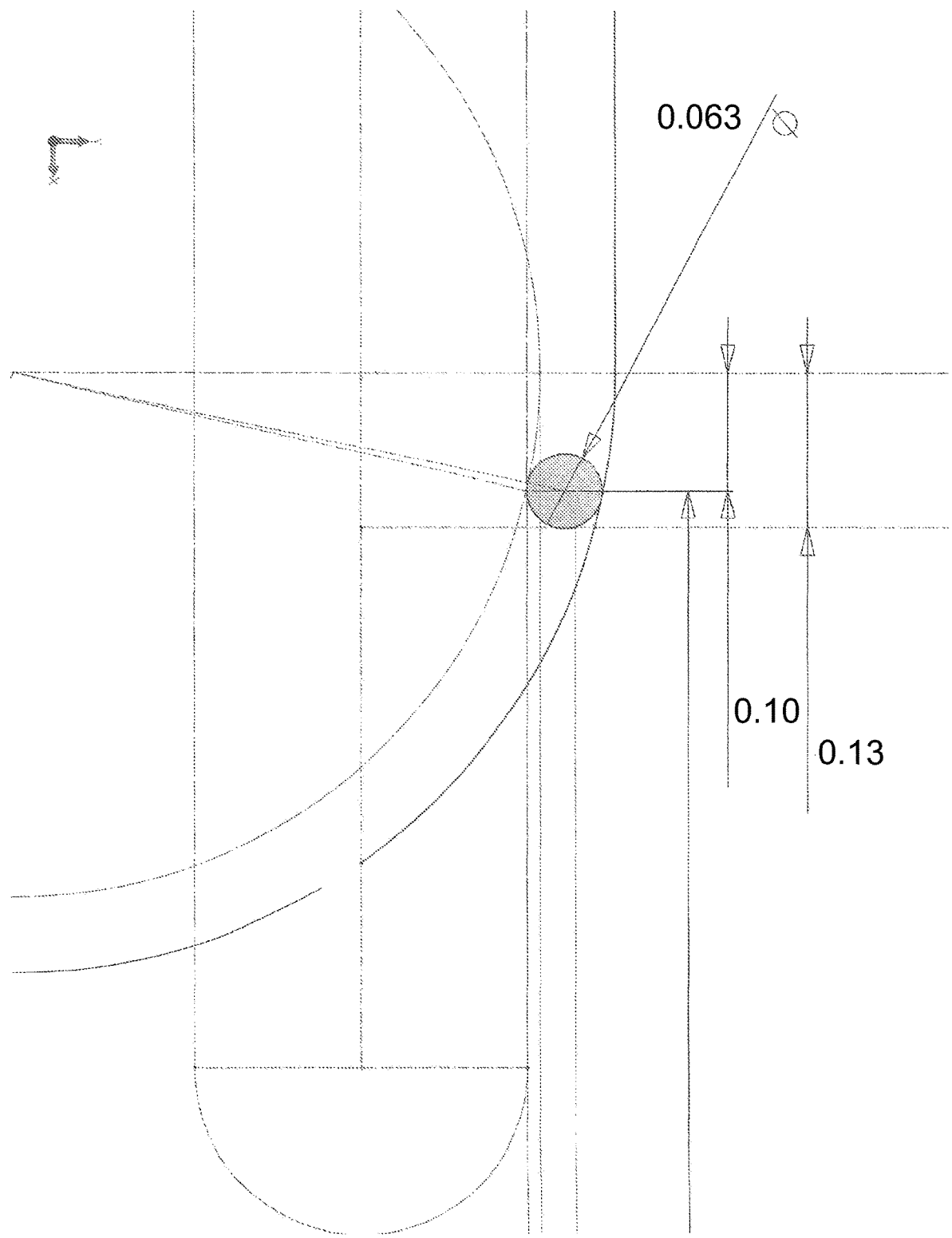
Figure 34:
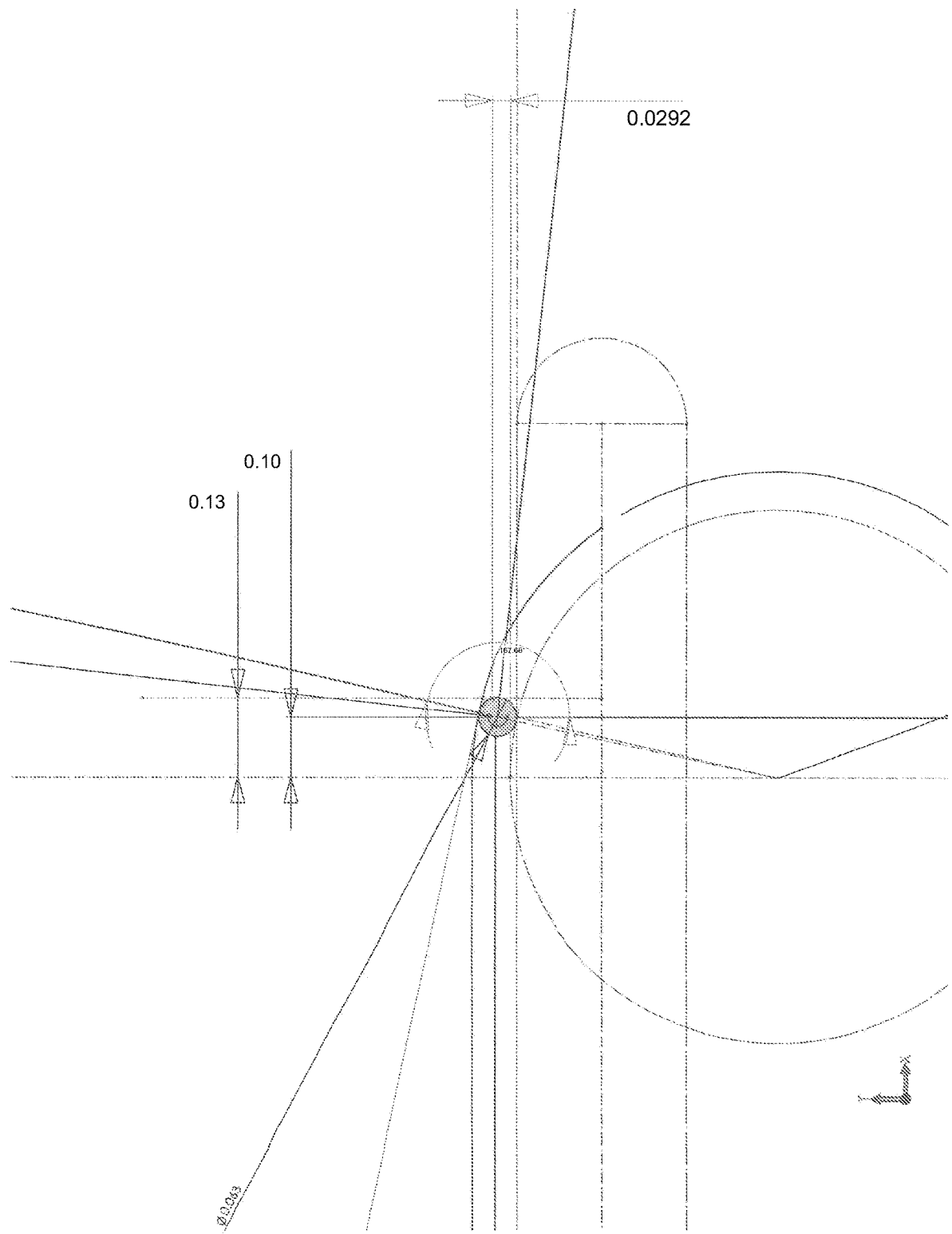

The opening structure 1 for a single glass ampoule 19 (FIG. 3) is shown in its side view 10 in FIG. 1, and in its front view 11 in FIG. 2, both shown in their assembled state. The opening structure 1 has a proximal end 8 and a distal end 9; has a substantially rigid housing 26 (FIG. 6), which is preferably made with plastic polymers, such as polyethylene. Also shown are opening methods of a twist-off, child-safety tab 7, a push button 2, and a dispenser/applicator tip consisting of a press-in connector 5, a dispenser applicator pad 4, and the applicator material 3 that directly applies the substance discharged from a broken glass ampoule, e.g. sponge. Integral to opening structure 1 are two press pads 6—one on top as shown in FIG. 2 and one opposite 180 degrees (not shown). For reference, approximate dimensions for the opening structure 1 and elements of the opening method are disclosed in FIGS. 21, 25A, and 27.

Figures 3, 4:
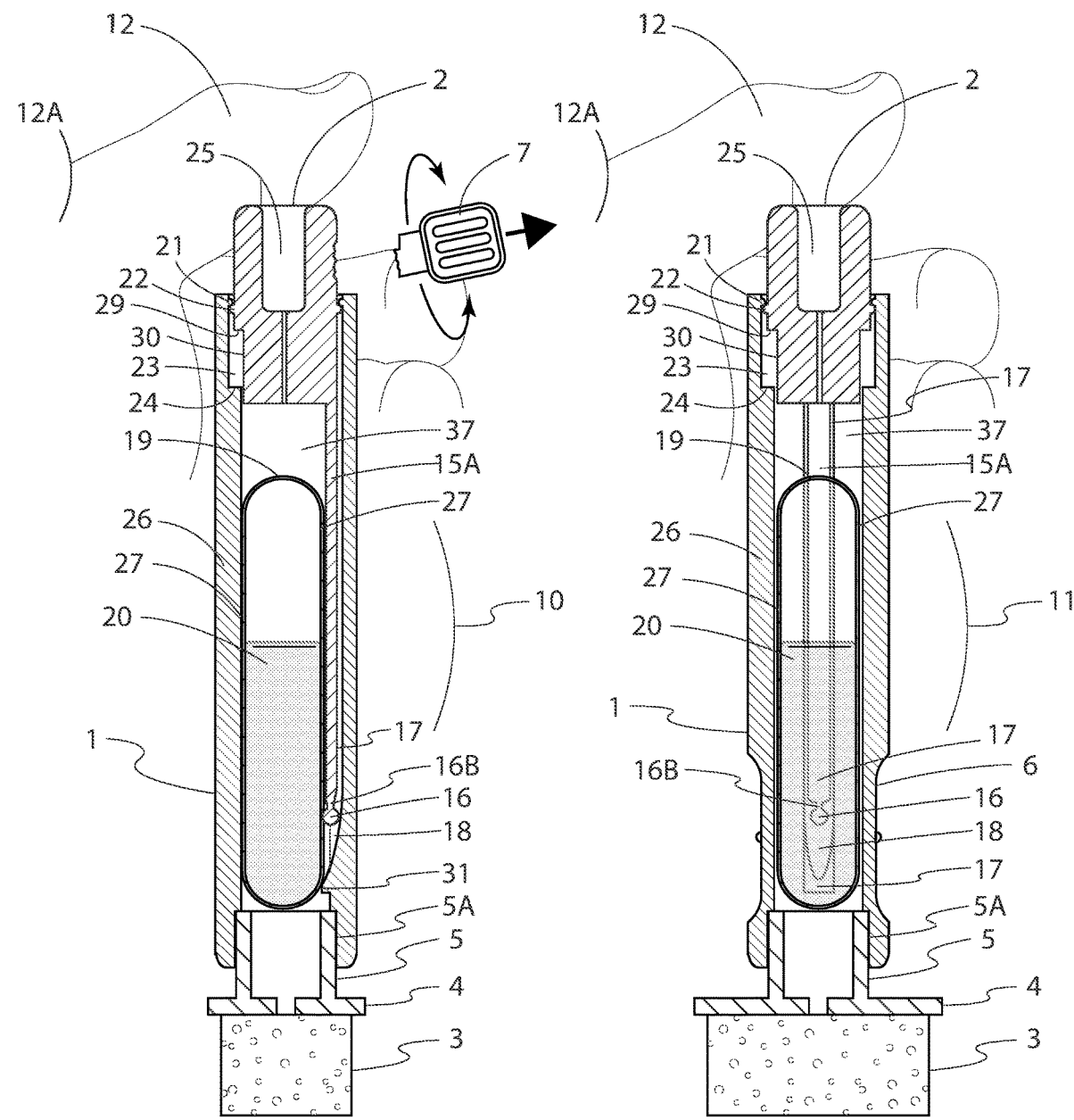
FIG. 3 is a cross-sectional side view of the opening structure showing operating elements of the opening method with a housed ampoule.
FIG. 4 is a cross-sectional front view of the opening structure showing operating elements of the opening method with a housed ampoule.

Now referring to further embodiments regarding the opening structure and opening methods: cross-sectional drawings in FIG. 3 and FIG. 4 show the opening structure 1 in both its front and side views. Opening methods consist of a twist-off child safety tab 7 removed by the user's hand 12A allowing the push button 2 to be pushed by the user's thumb 12. The push button 2 has an external sealing surface 22, which provides an airtight guidable fitment once it is pressed into housing 26 (FIGS. 3 and 4). Sealing surface 21 is the internal sealing surface of housing 26, and assists in providing an airtight and guidable assembly. Push button 2 is shown with a vent port 25, which is not always required. Sometimes it is preferred to have a vent port 25 when the substance in the ampoule is viscous and the press pads 6 will be cycled repeatedly to expel the ampoule's viscous substance.

The user's thumb 12 will apply approximately four (4) pounds-force to fully activate push button 2, which is the preferred specification for a user-friendly push button, and meets the Department of Defense Design Criteria Standards: MIL-STD 1472F. The push button 2 has a stepped-in bearing surface 30 that contacts the internal wall surfaces 27 of housing 26, and upon completion of the push button's travel within the travel distance space 23, it will stop at the housing ledge 24.

Ampoule 19 is shown enclosed within housing 26 with voided air space 37, and rests on bottom ledge 31 located at distal end 9. The ampoule 19 has substance 20 filled to approximately one-half of the ampoule's holding capacity. Push button 2 has an integral telescopic push-rod 15A that has a spherical ball 16 attached by tether 16B having a diameter of 0.0625 inches. Push-rod 15A travels linearly within the housing's internally recessed guide channel 17 that has a rounded internal section 18 at its distal end 9.

When push button 2 is fully depressed wherein stop 29 has reached housing ledge 24, a travel distance of approximately 0.250 inches, the telescopic push-rod with tethered spherical ball 16 has been forced into the ampoule 19 with an approximate pounds-force of 18.6 precisely at the point the spherical ball 16 ends its downward movement at rounded surface 18. The tethered spherical ball 16 travels an inward thrust distance (from the housing's internal wall 27) of approximately 0.080 inches.

Figure 6:
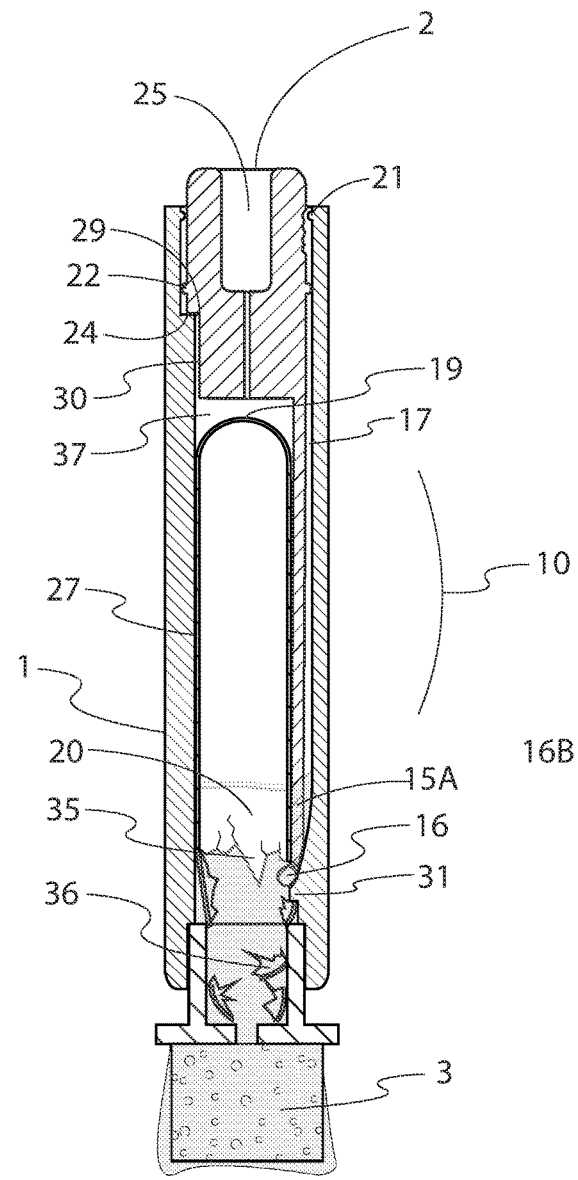
FIG. 6 is a cross-sectional side view of the opening structure showing operating elements of the opening method upon breaking a single glass ampoule.
Figure 7:
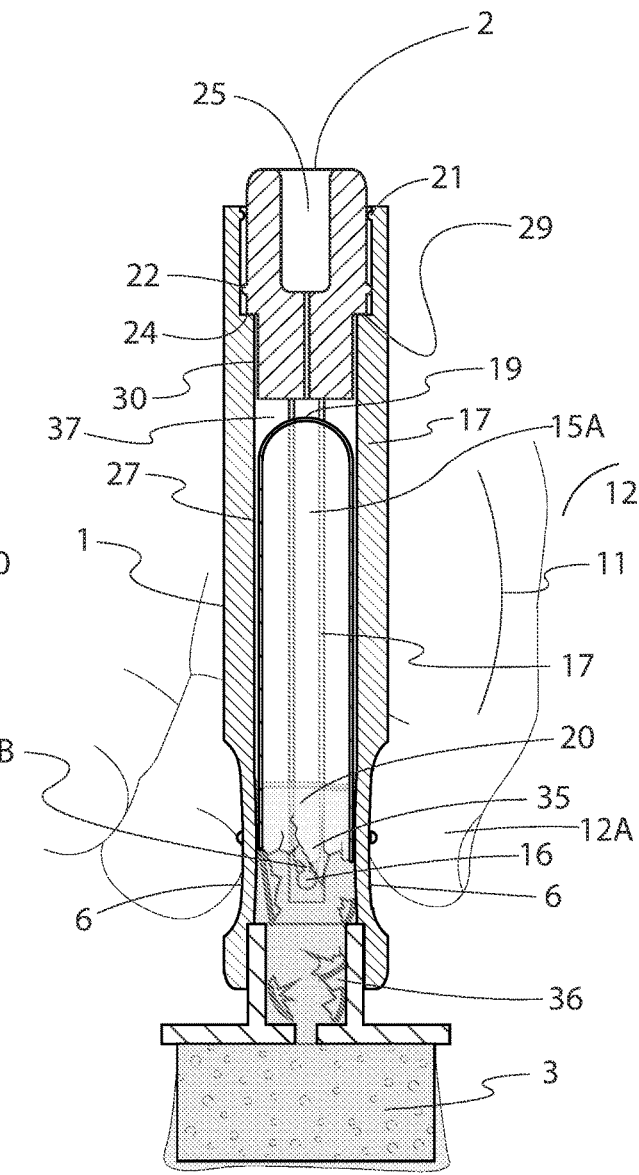
FIG. 7 is a cross-sectional front view of the opening structure showing operating elements of the opening method upon breaking a single glass ampoule.
Figure 25B:
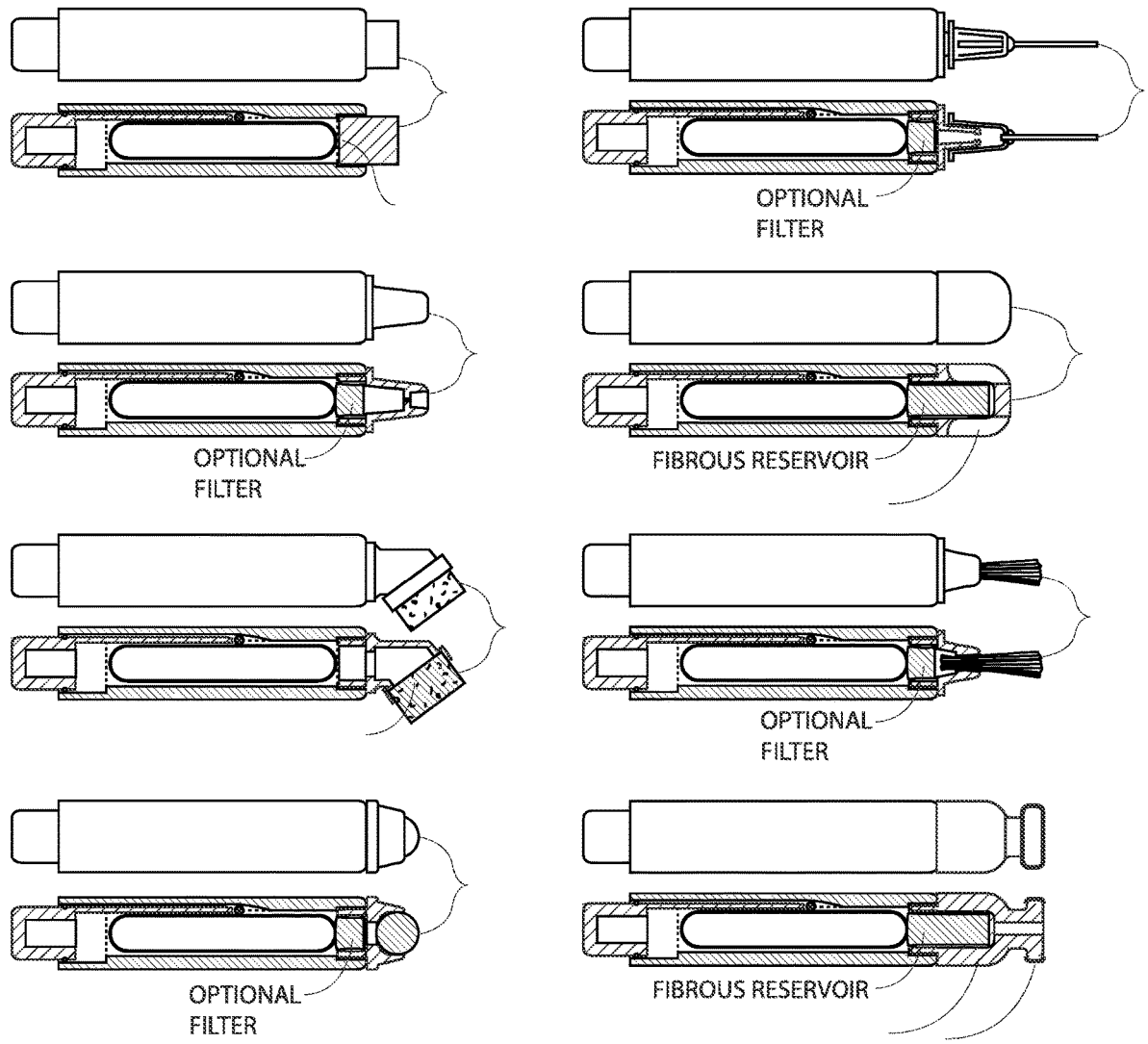
FIG. 25B presents drawings in their side views depicting the opening structures various dispenser/applicator tips.

Now referring directly to FIGS. 6 and 7, the embodiments relative to the opening methods and elements regarding the breakage of ampoule 19 and the discharge of its contained substance to the dispenser/applicator material 3 will be described. As can be seen in FIG. 6, the tethered spherical ball 16 has fractured the glass ampoule 19 adjacent bottom edge 31, allowing the substance 20 to flow unrestricted and freely to the dispenser/applicator material 3, wherein the bottom part 36 of the ampoule 19 shows that a small amount of glass fragments remain in the discharge area defined by connector 5 (FIG. 3). Testing has shown that approximately 20% of the ampoule's total glass content (shown in FIG. 25) of the ampoule before breaking falls into the discharge area, and that approximately 80% of the ampoule's original glass content remains structurally intact, and above the break point at ledge 31 of the glass ampoule, as shown in FIGS. 6 and 7. The glass content above where the ball 16 has fractured ampoule 19 are shown at 35 and the fractured area of ampoule 19 are shown at 36. Because the ampoule 19 is snuggly held by the interior wall surfaces 27 of housing 26, the ampoule's upper section, representing approximately 80% of the ampoule's glass content, remains in the same position as prior to breakage. FIG. 7 shows the user's thumb 12 pressing the press pads 6 to facilitate the delivery of substance 20 to the applicator material 3.

Figure 5:
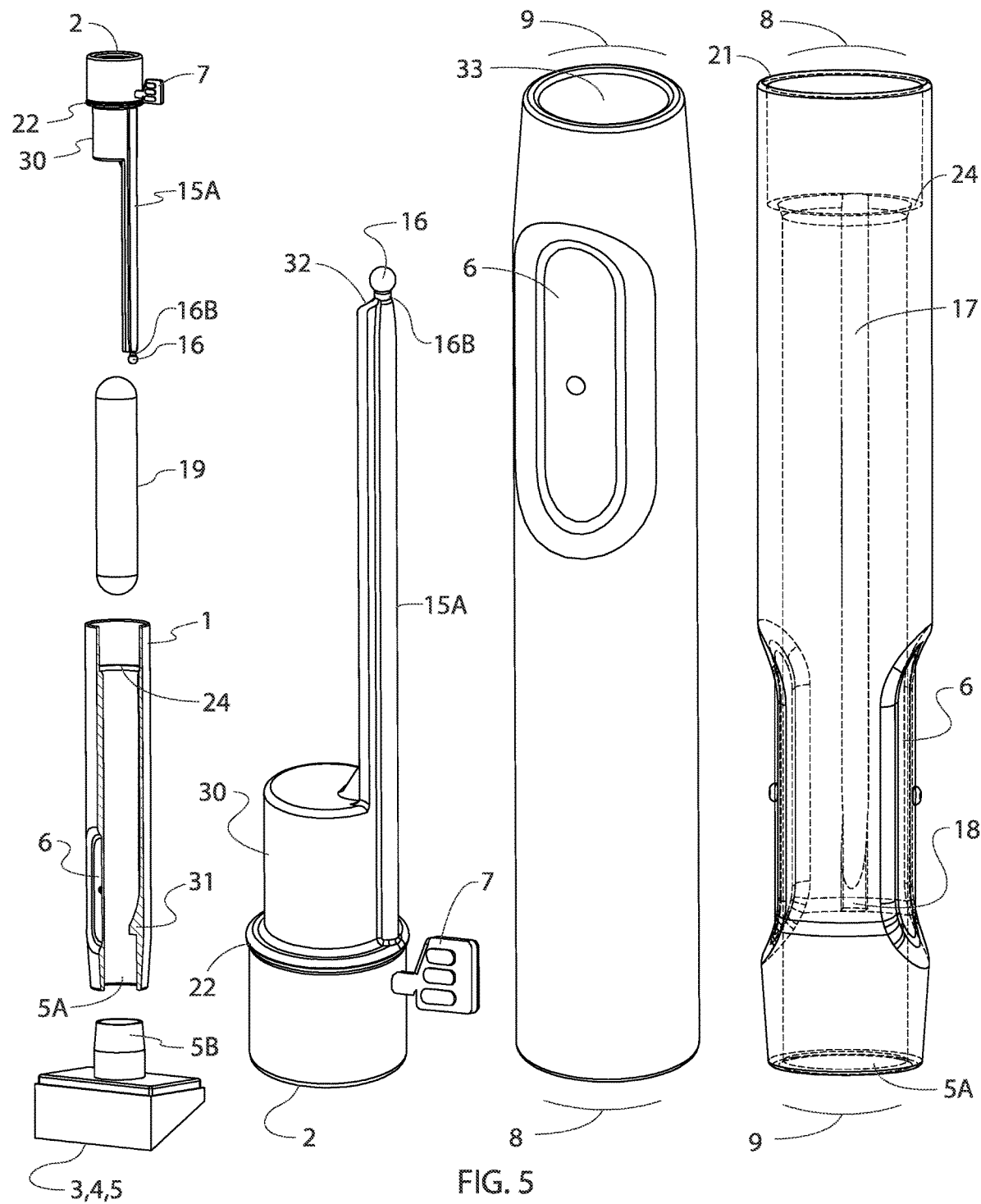
FIG. 5 are orthographic and exploded views of the opening structure and elements of the opening method.

FIG. 5 represents orthographic exploded views of the opening structure and opening elements described above.

Figures 8, 9, 10:
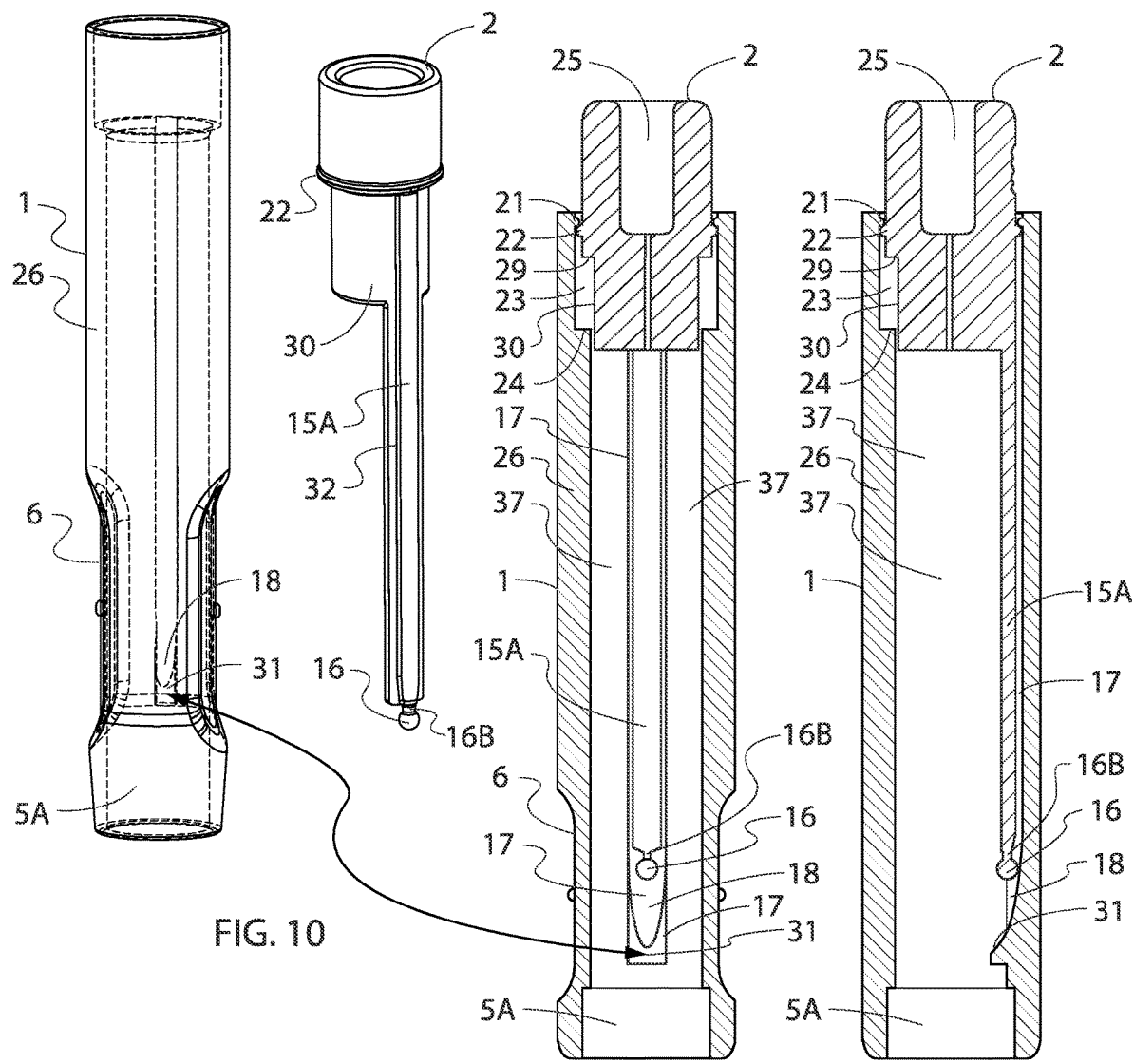
FIG. 8, is a cross-sectional front view showing further detail relative to embodiments of the opening structure and elements of the opening method.
FIG. 9 is a cross-sectional side view showing further detail relative to embodiments of the opening structure and elements of the opening method.
FIG. 10 is an orthographic side view showing by way of hidden lines the internal opening structure.

FIGS. 8, 9 and 10 show key element embodiments of the push button 2 having a seal surface 22 with a push-rod 15A having channel guides 32, bearing surface 30, spherical ball 16, and tether 16B. Additional views of the housing's internal guide channel 17, the rounded kick-in surface 18, and positioning ledge 31 are shown. Push button 2 and its connecting components are preferably manufactured from the plastic polymer Delrin, and/or some type of polycarbonate.

Figure 11:
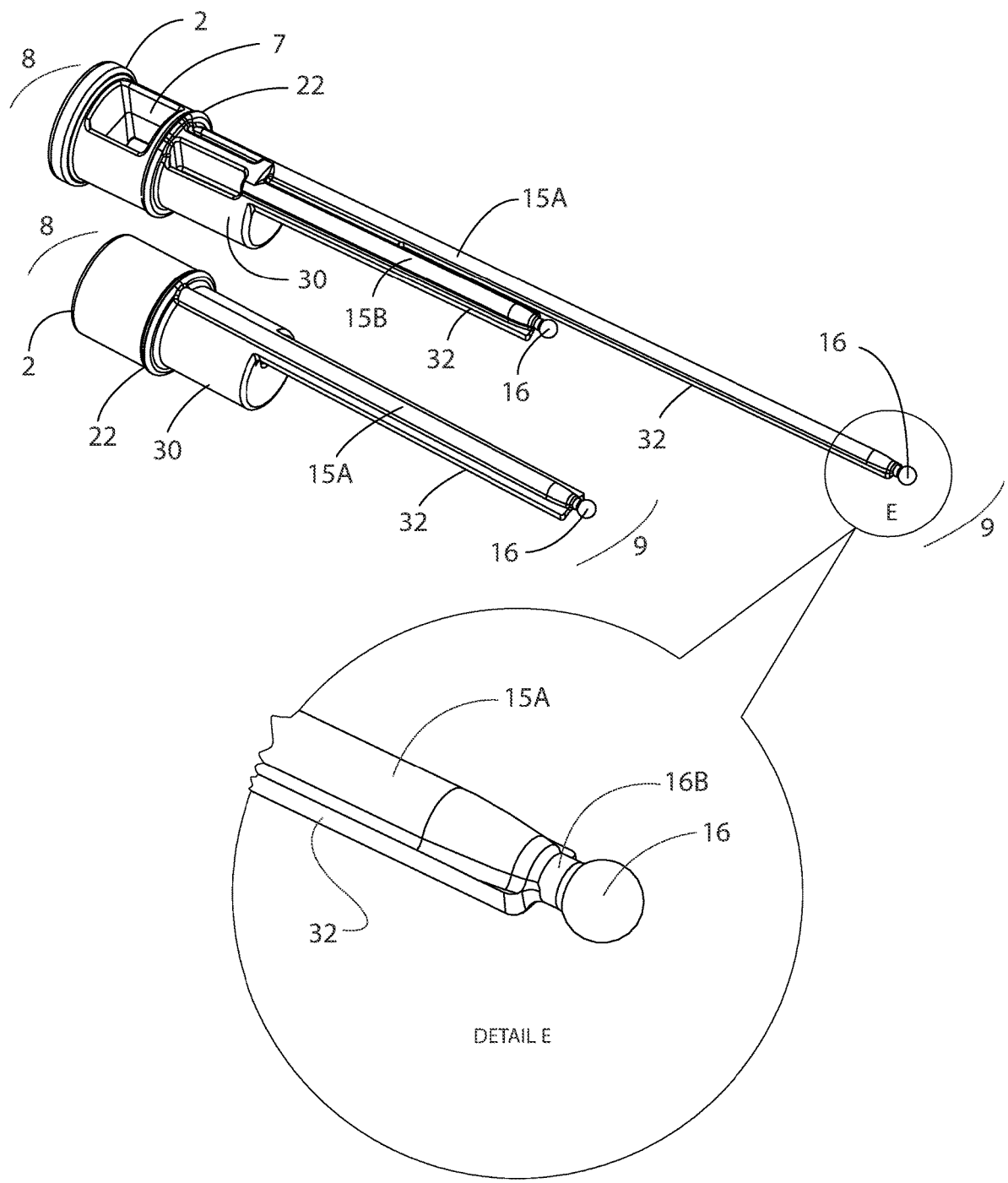
FIG. 11A are orthographic views showing details of various push button assemblies incorporating the push-rod sub-assemblies.
FIG. 11B presents orthographic views showing the details of the push button/push-rods incorporating two different ampoule breaking means; one a free rolling ball, the other having a razor type sharp edge.
Figure 11A:
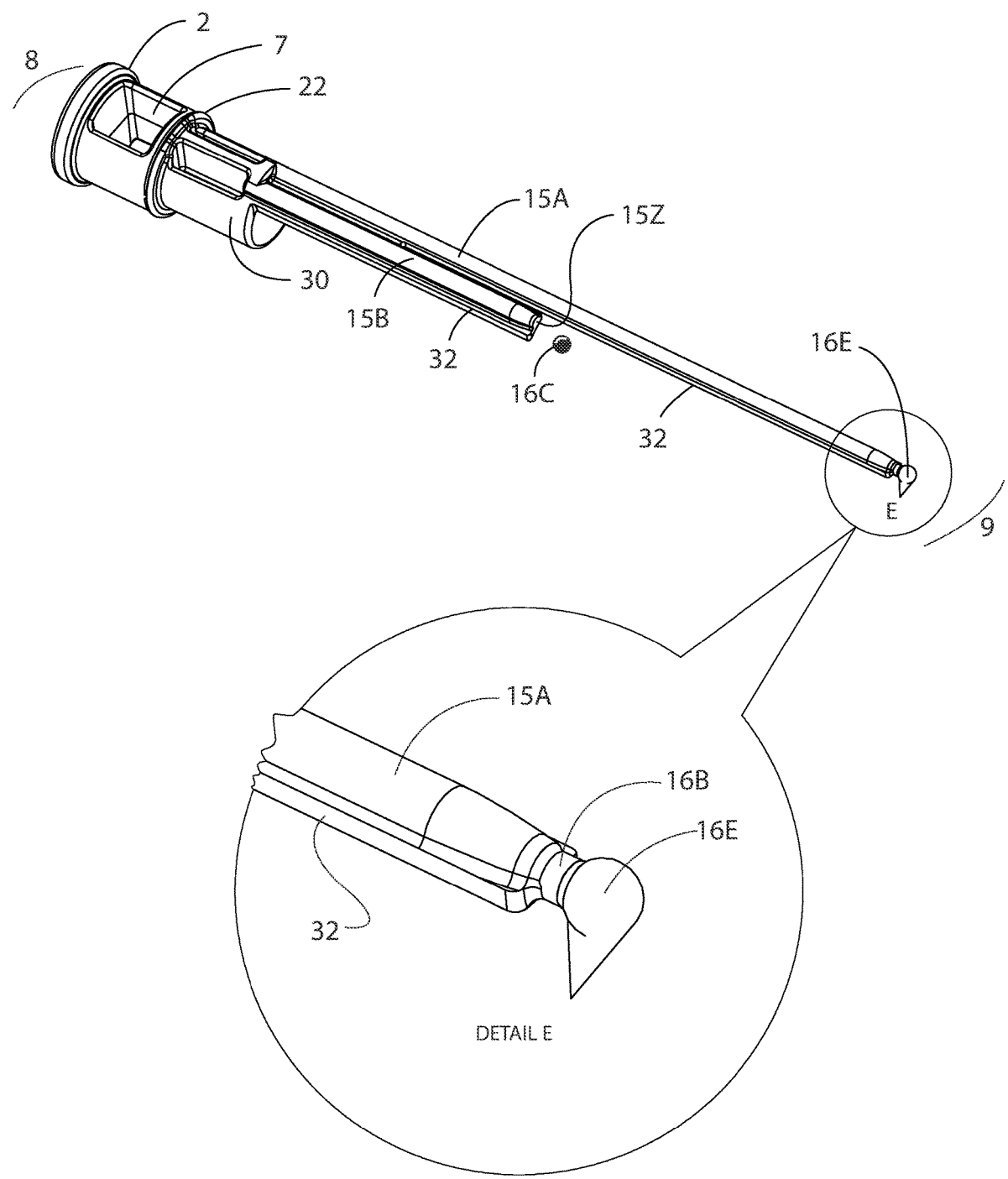

FIG. 11A represents orthographic detailed views of push button 2 and its connected push-rod 15A. An enlarged Detail E view of the push-rod's 15A construction detailing the push-rod 15A, push-rod male guides 33, tether 16B and spherical ball 16.

Figure 12:
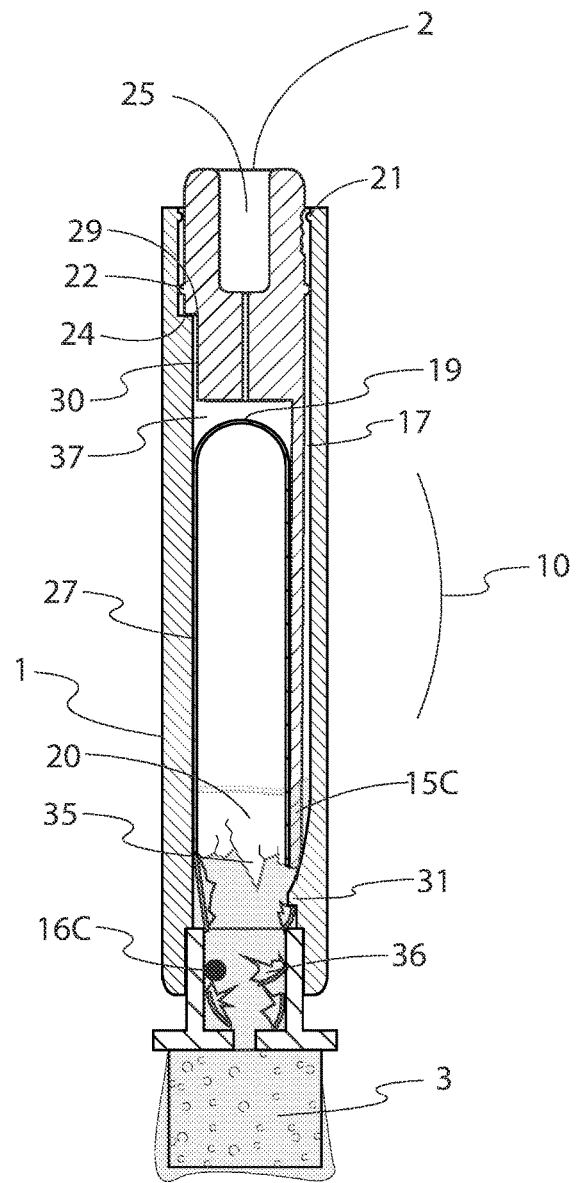
FIG. 12 is a side view of the opening structure showing the proximal and distal ends of a dual-ampoule opening embodiment.
Figure 13:
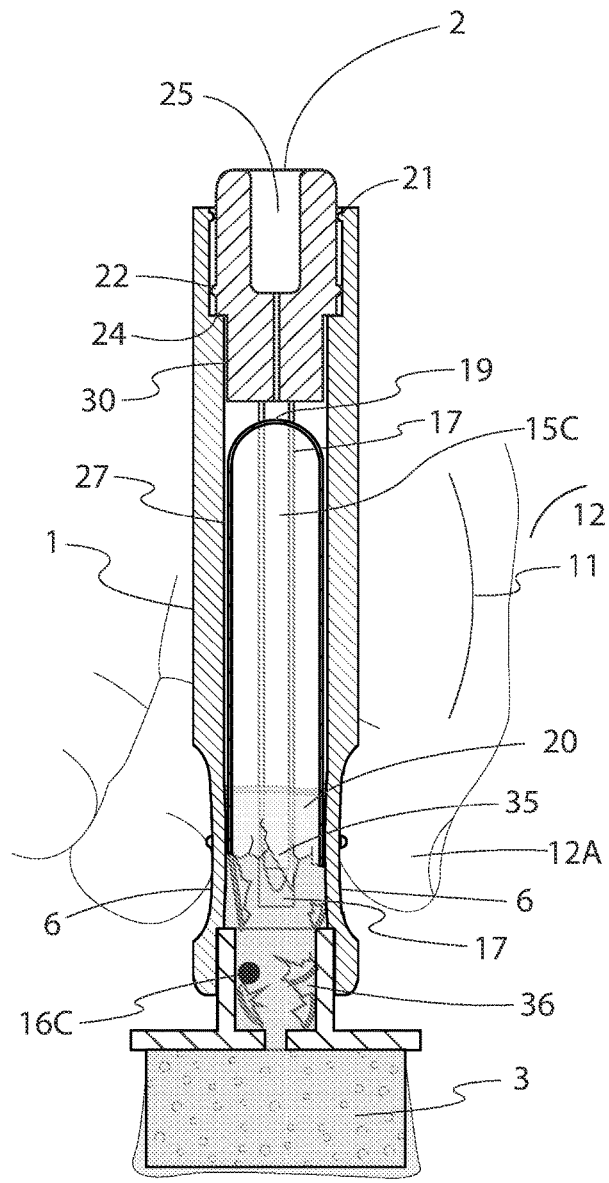
FIG. 13 is a cross-sectional front view of the opening structure showing operating elements of the opening method upon breaking a dual ampoule configuration embodiment.

Another preferred embodiment will now be described. In some applications the glass ampoule is constructed with a thicker protective glass because it contains a biological sample, a medicament, etc., which may require special sterilizations, etc. In such applications, the opening structure and opening methods can be utilized as shown in FIGS. 12 and 13. Opening structure 1 and housing 26 remain the same as previously described. The opening method element of the push button 2 and its connected telescopic push-rod 15A remain the same, but the tethered spherical ball has been removed and replaced with a free-rolling steel or ceramic type ball 16C. Push button 2 is depressed and the telescopic push-rod 15C pushes the rolling ball 16C (approximate diameter of 0.0625 to 0.125) to the rounded kick-in ledge 31 to thrust the free rolling ball 16C inward into the glass ampoule 19 at ledge 31. This fractures the ampoule at the same location and with the same benefits as previously described regarding the opening structure and opening methods and elements.

Figure 14:
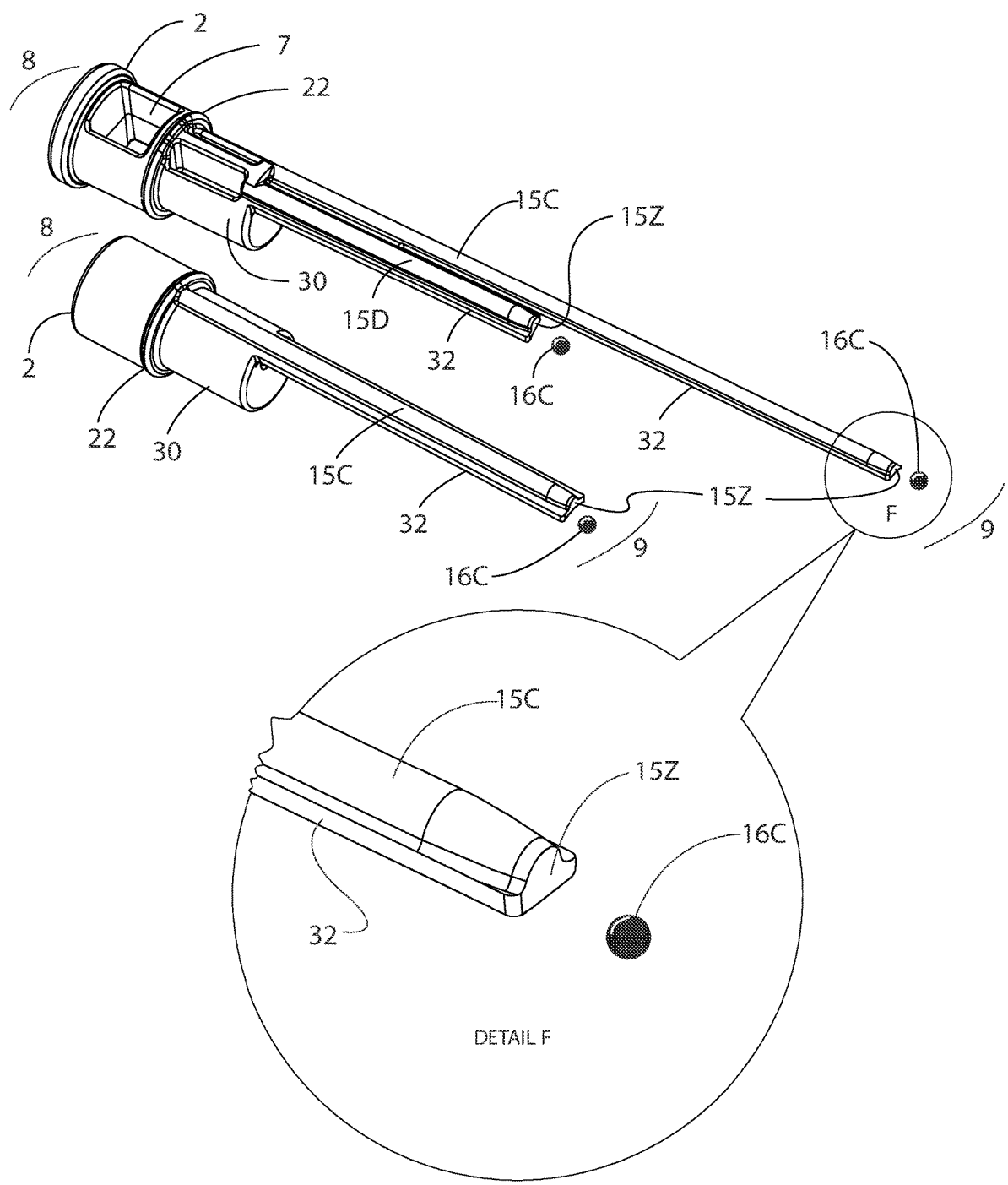
FIG. 14 are orthographic views of the push-rod utilizing a free-rolling ball arrangement.
Figure 15:
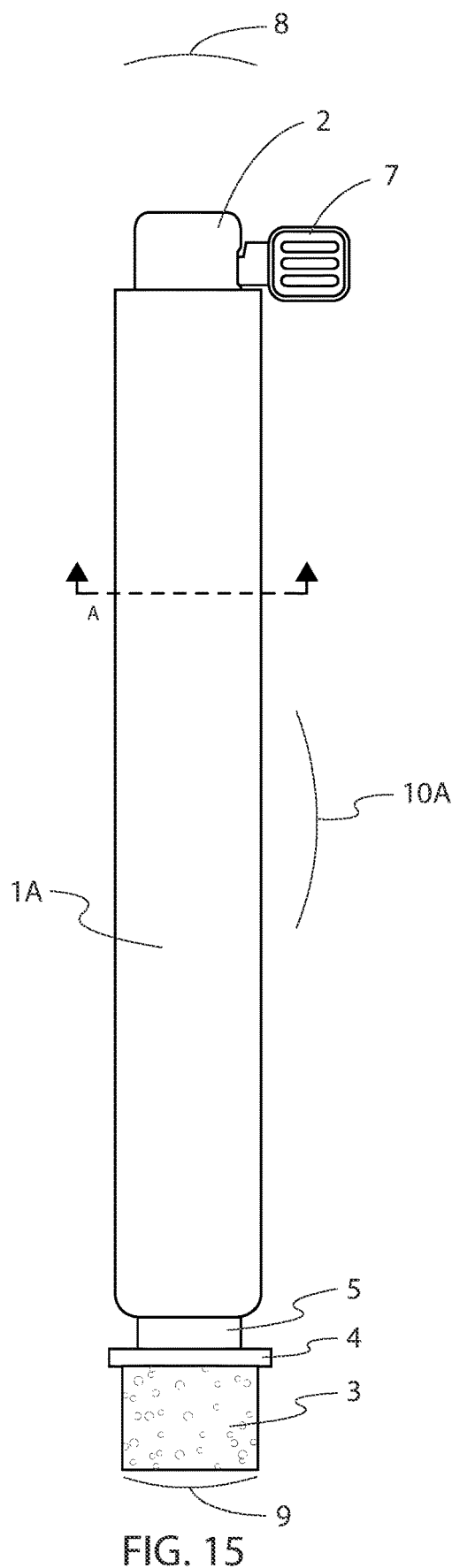
FIG. 15 and FIG. 16 show the side and front views of the opening structure containing multiple ampoules.
Figure 16:
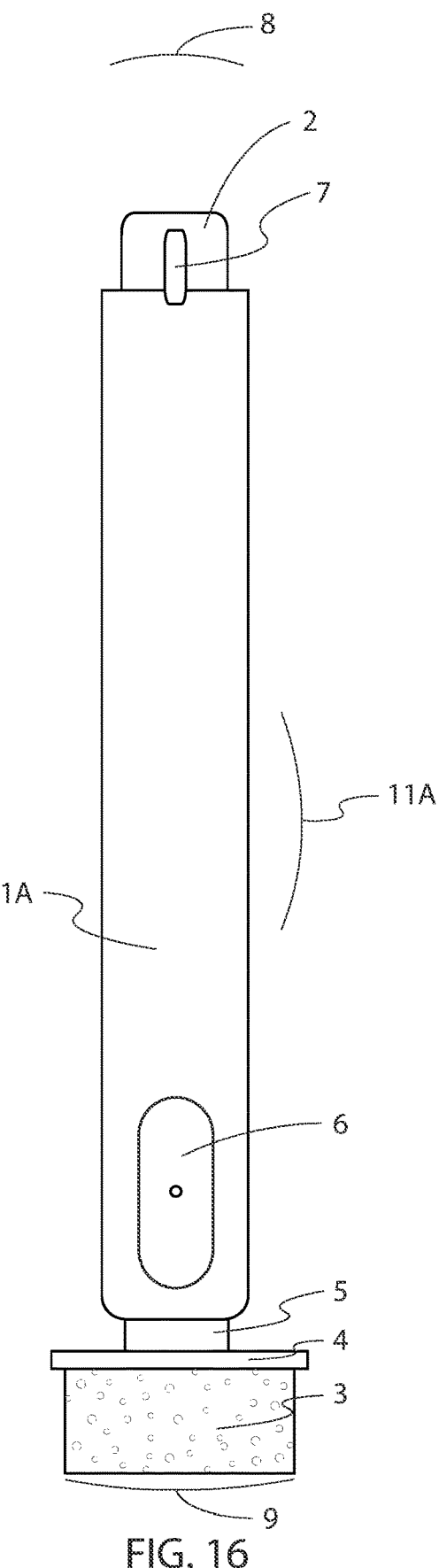
Figure 17:
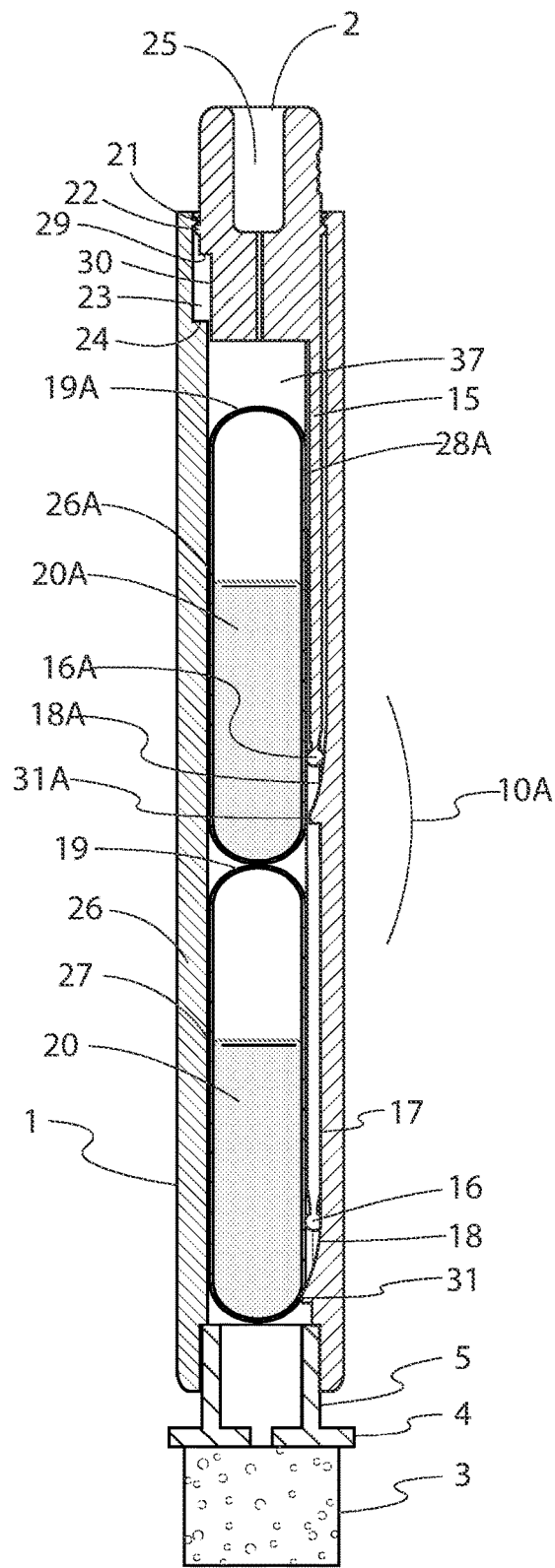
FIG. 17 and FIG. 18 are side and front cross-sectional views of a multiple ampoule opening structure.
Figure 18:
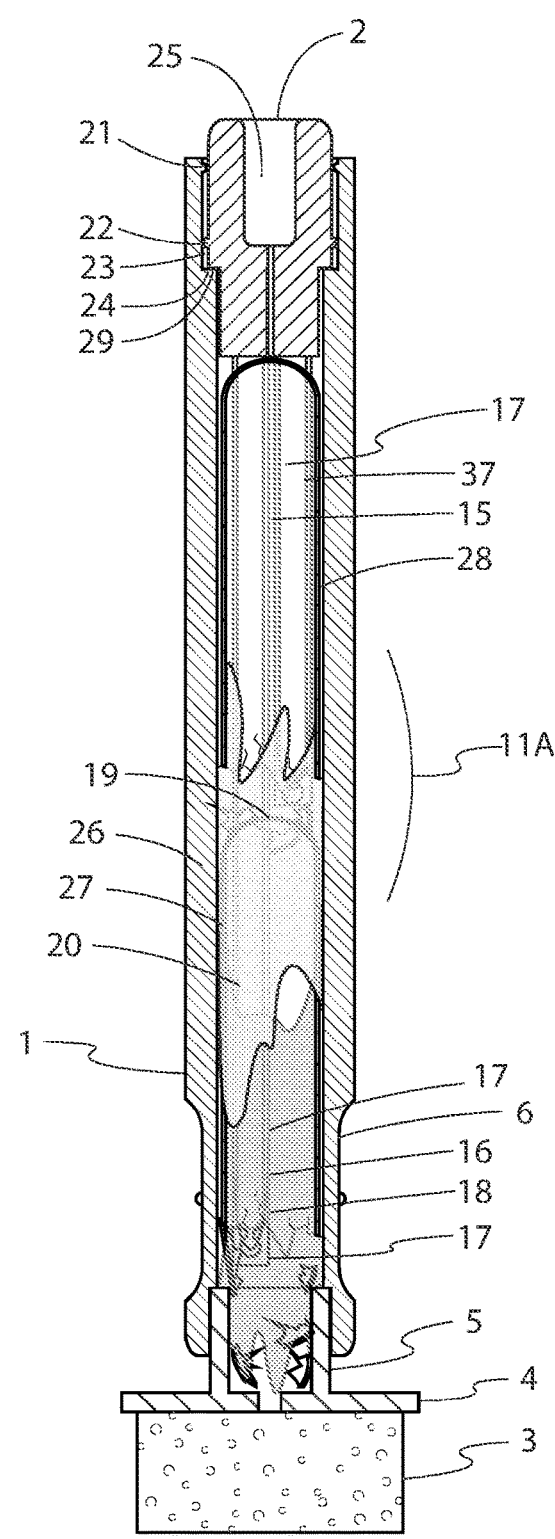

FIG. 14 shows orthographic drawings depicting push button 2 and push-rod 15C for use with a single ampoule housing, as well as push-rod 15D and push-rod 15C collectively for use with a dual ampoule housing. All push-rods, whether a single ampoule or a dual ampoule, will use the same type of free-rolling steel ball 16C which is pushed by the push rod(s) exterior distal end 15Z to the kick-in ledge 31 (FIGS. 12 and 13).

FIGS. 15-18 show another unique embodiment of having a larger housing 26, which supports two independent ampoules 19 and 19A. The opening methods and elements described earlier for the single ampoule "breakage" are basically replicated to facilitate a dual ampoule breakage. A single push button 2 has dual telescopic push-rods represented by the top push-rod 15 and bottom push-rod 15A. Each push-rod has a tethered, spherically-shaped ball 16 and 16A, respectfully.

Figure 22:
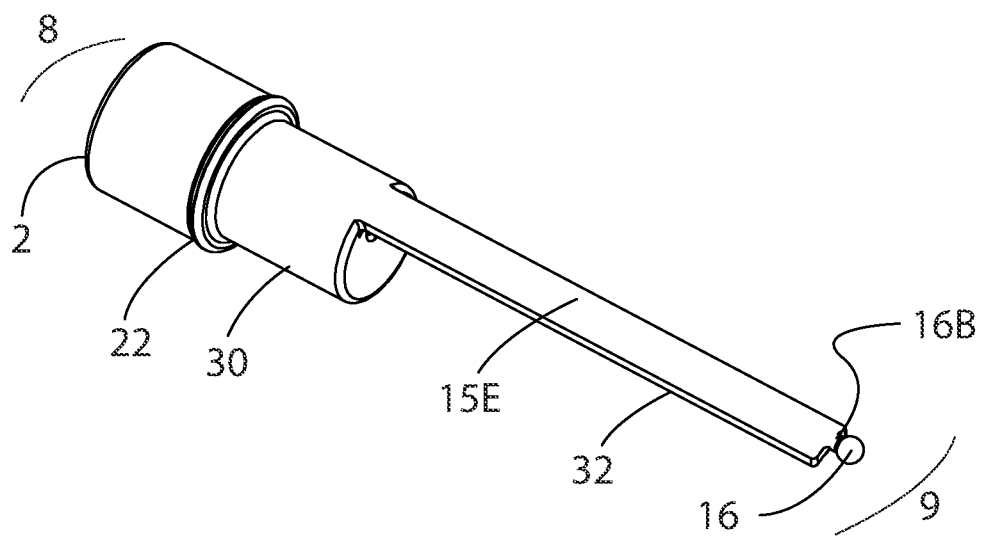
FIG. 22 are two orthographic views of the push button/push-rod assembly utilizing a tethered ball, and a free-rolling ball.
Figure 22:
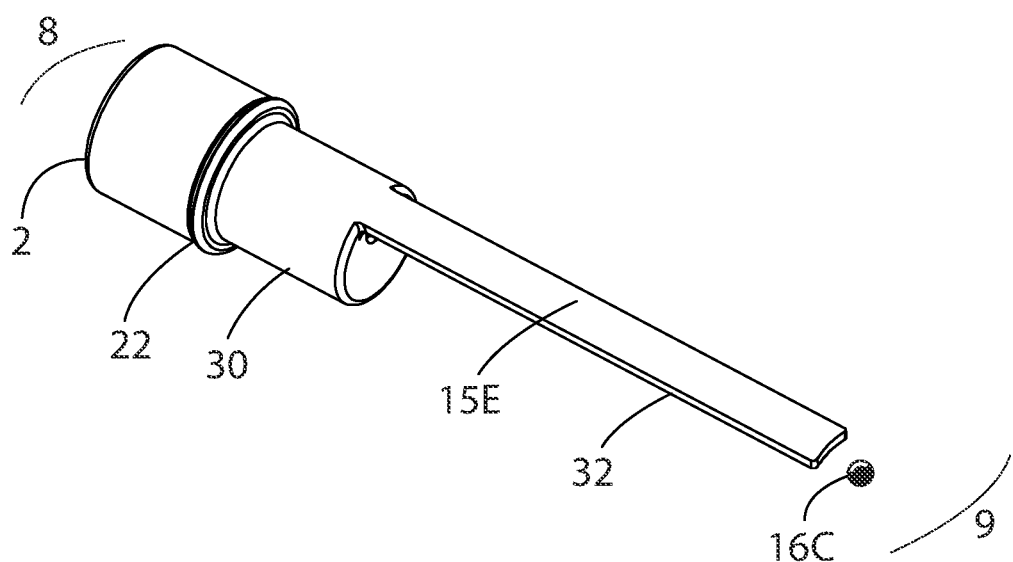

FIGS. 19-22 further show embodiments using the opening structure 1 and opening methods and elements of the invention to provide delivery of a substance from an ampoule 19 having a protruding neck 38, and that receives a syringe 47 type device for extraction of fluid 50. Ampoule 19 is positioned with its base located in the distal end 9 of the opening structure 1. The push button has a telescopic type push-blade 15E that is shaped to fit closely to the interior wall of housing 26 (concave shaped). Push blade 15E linearly travels without the need for an interior guide channel as described in previous embodiments. Push-blade 15E includes a tethered spherical ball 16, or can be used as a ram with a free-rolling steel or ceramic type ball arrangement (FIG. 22). In operation, the syringe needle pierces a self-sealing septa 41, which is held to housing 26 and sealed by a crimp-on top 42. Filtering material that the syringe needle extracts the ampoule's fluid from is represented by 49. A syringe needle guide channel is identified as 43. The special dispenser outlet assembly 39 is press fitted into the receptacle 46.

Figure 23A:
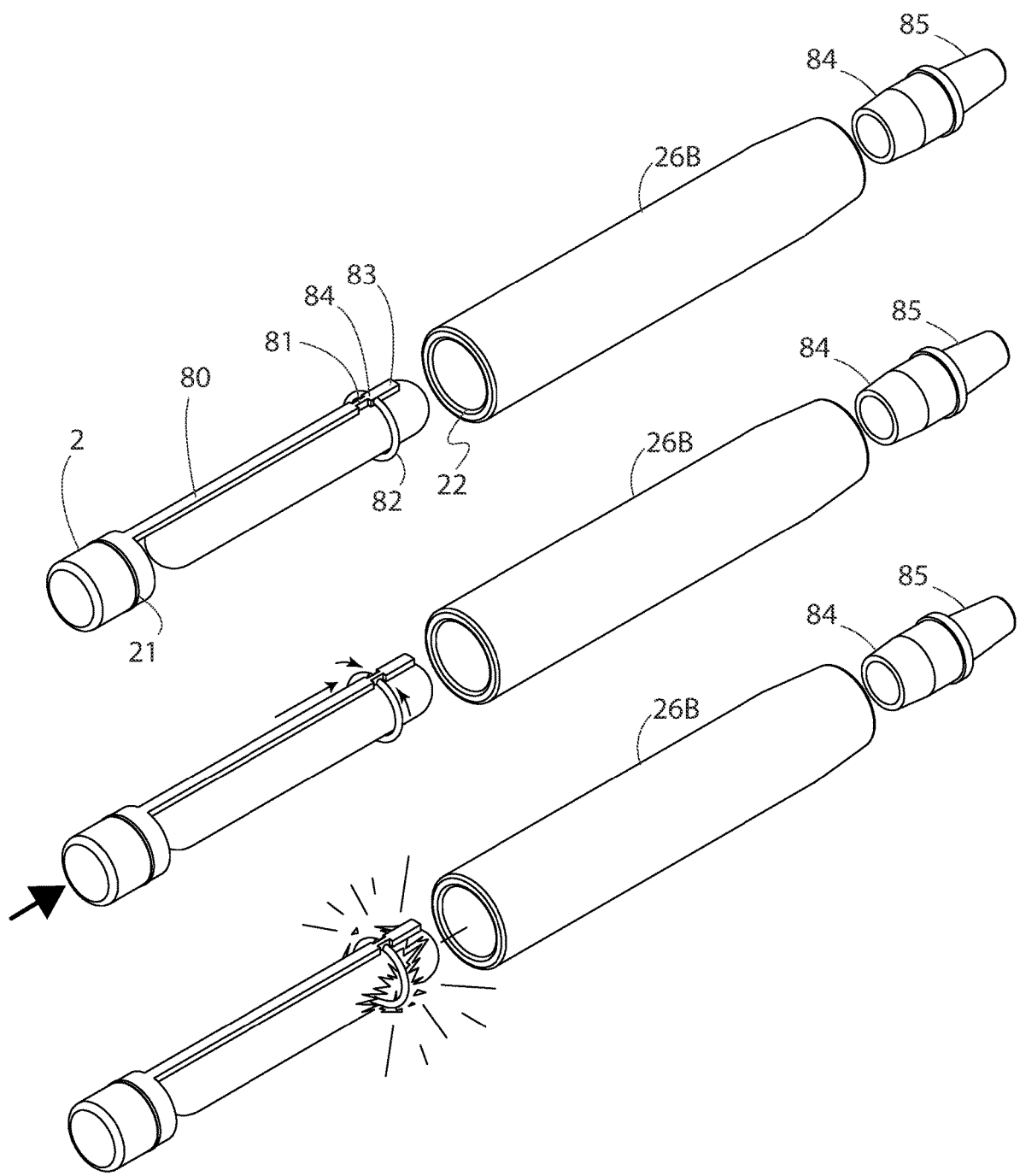
FIGS. 23A and 23B present orthographic views of a compressed internal snap ring ampoule-fracturing embodiment.
Figure 23B:
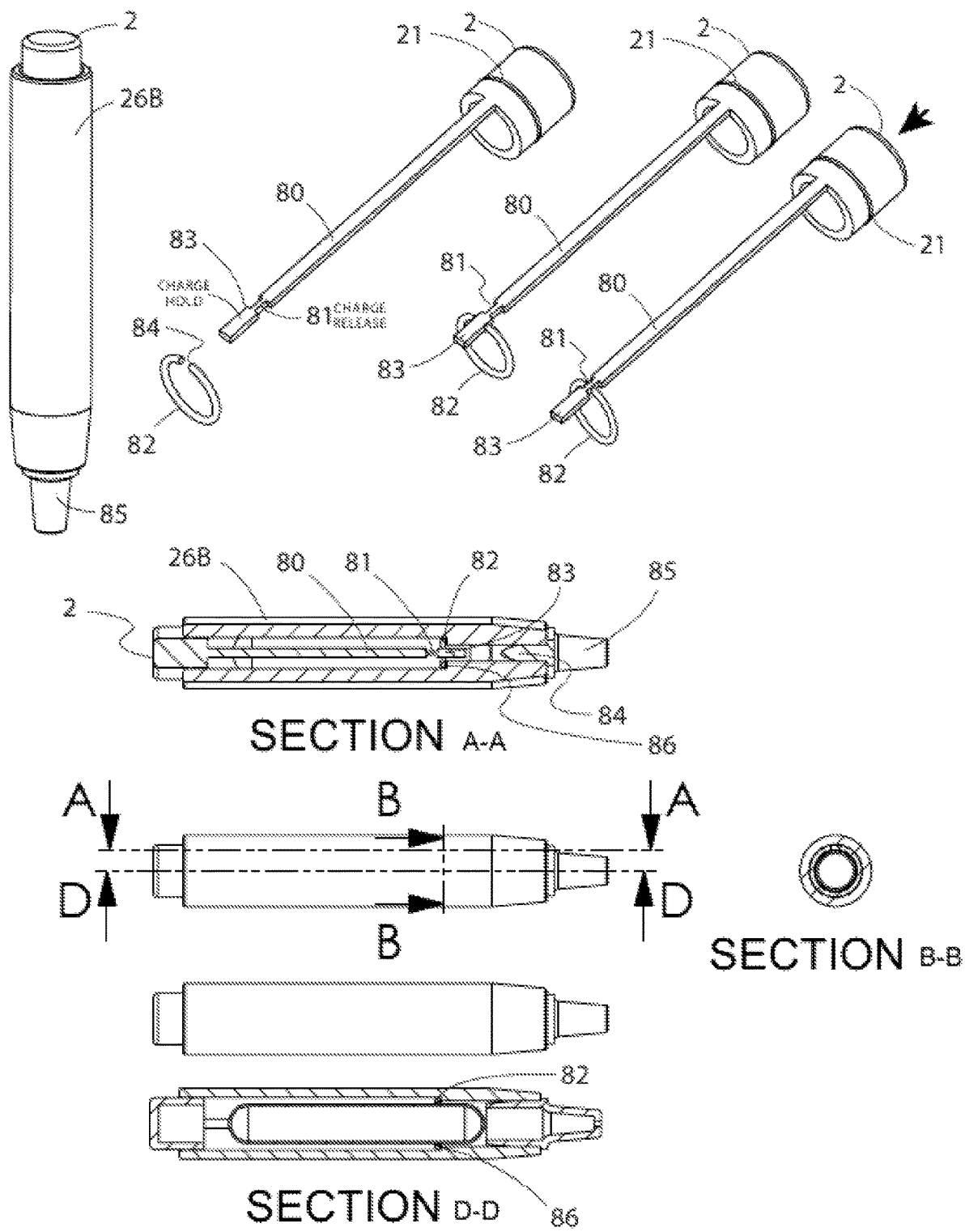

A further preferred embodiment, shown in FIGS. 23A and 23B, includes an economical simple opening method to fracture a substance filled glass ampoule 19 by simply providing a releasable internal snap ring 82 that is under compression, and allowing the internal type snap ring to fracture the glass circumferentially. This embodiment would have utility as an inhaler (e.g. ammonia) where housing press pads would not be required. The fluid is retained by a liquid holding chamber containing a fibrous sponge-like reservoir immediately proximal of the vapor release tip 85. Only vapor is released. No liquids are expelled. Glass fragments remaining after fracture have no influence on the flow of vapor from dispenser vapor release tip 85. The dispenser has an opening structure housing 26B; a liquid holding chamber 84; a vapor releasing tip 85. The glass ampoule 87 has a resting ledge internally within the housing 26B, and is positioned within a push-rod assembly having a telescopic arm 80 which has an integral shoulder 86 towards its distal end 83 that retains a compressed internal type snap ring 82, (top drawing). Upon push button 2 (FIG. 23B) being depressed, arm 80 extends linearly and distally from the shoulder 86, causing the internal snap ring to be released from compression by release area 81 (charge release) on the arm 80 to circumferentially crush the ampoule (middle drawing).

Figure 24A:
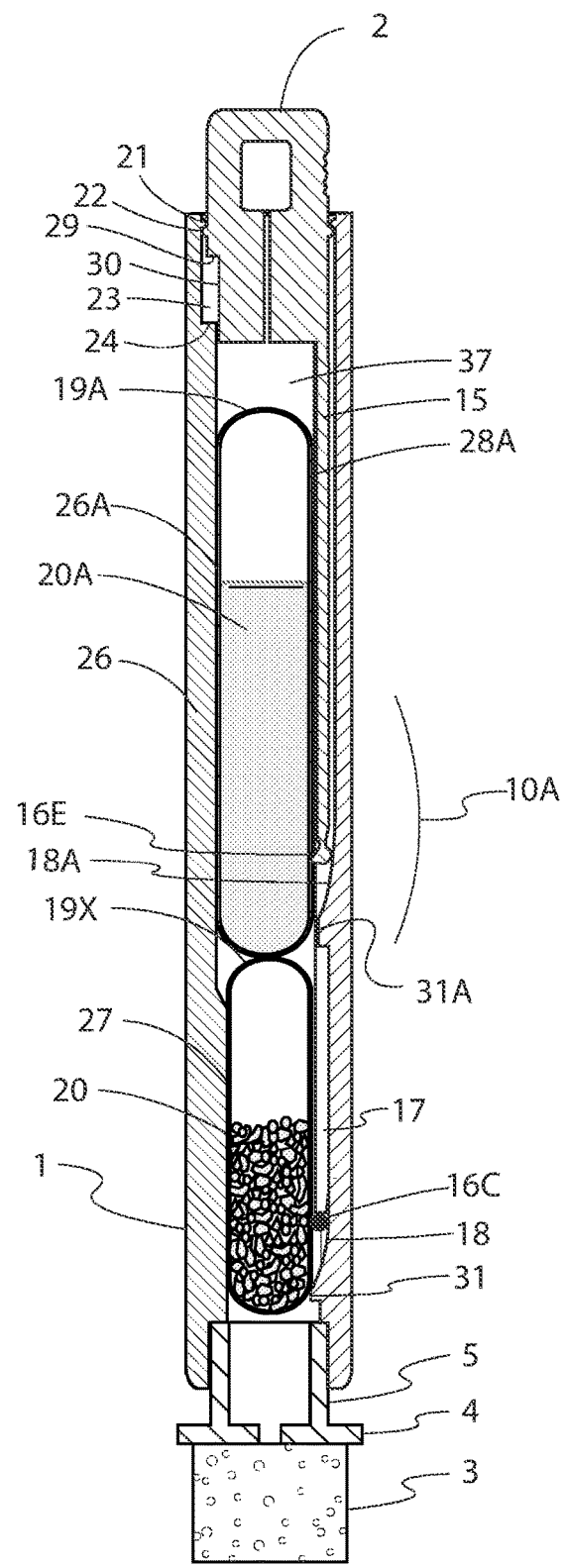
FIGS. 24A and 24B are orthographic views of an opening structure containing multiple ampoules having different substances and different ampoule sizes; and, different ampoule opening means.
Figure 24B:
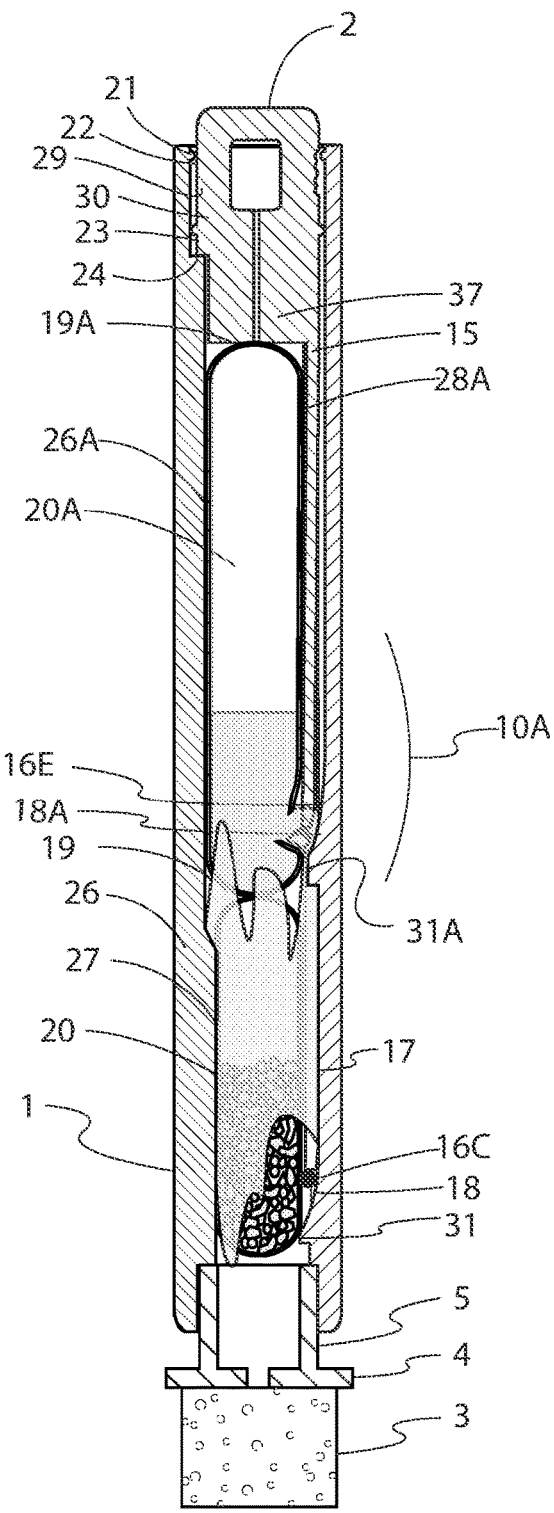

Further to additional benefits of the invention, various embodiments are shown in FIGS. 24A and 24B wherein housing 26 contains two different size ampoules, each containing different substances. The ampoules are fractured, pierced and/or broken in a staggered sequence upon activation of the push button, e.g., the top ampoule contains a liquid and the bottom ampoule contains a powder. The top ampoule has a larger diameter and longer length than the bottom ampoule. Ampoules may be glass as shown, or can be made of plastic, metal foil, etc. One of the breaking means, shown at 16E, utilizes a tethered ball arrangement in which the ball includes a point positioned to contact the ampoule to enhance breakage. Ampoule breaking means could also include the embodiments previously described herein. Additionally, a piercing element could be utilized instead of the ball type(s) arrangement when the ampoule container is made of a piercable type of material.

An additional embodiment can be seen in FIG. 11B, which shows the versatility of the invention. Push button 2 has a stackable safety tab 7 that will prevent accidental activation of the push button 2. Push button 2 has a dual push rod arrangement wherein the long push rod 15A has a piercing edge or point for breaking a plastic ampoule that is located in the lower section of the housing. The shorter push-rod 15B has a free-rolling steel or ceramic type ball for fracturing a glass ampoule located in the upper section of the housing on 31A.

A latitude of modification, change and substitution is intended in the foregoing disclosure, and in some instances some features of the invention will be employed without a corresponding use of other features. Therefore, since many possible embodiments may be made of the invention without departing from the scope thereof, it is to be understood that all matter herein set forth or shown in the accompanying drawings is to be interpreted as illustrative and not in a limiting sense.

In an embodiment, the opening device comprises a housing adapted to receive a frangible ampoule and having a proximal end and a distal end; a push-rod received within the housing within a clearance space between the housing and an ampoule received therein, the push-rod being axially movable in the distal direction from a proximal position in which an ampoule received within the housing is intact, to a distal position in which an ampoule received within the housing has been opened; a push button attached to the push-rod and having a portion exposed outside of the proximal end of the housing for contact by a user of the opening device, the push button being depressible distally relative to the housing and thereby moving the push-rod from the proximal position to the distal position; and a ball adapted to be moved axially by axial movement of the push-rod from the proximal position to the distal position, the ball having a proximal position in which the push-rod is in its proximal position and in which an ampoule received within the housing remains intact, the ball having a distal position in which the push-rod is in its distal position and in which an ampoule received within the housing is broken open, the housing defining a distal guide portion which is ramped inwardly toward an ampoule received in the housing, the guide portion being configured to force the ball to move inwardly as it moves axially from the proximal position to the distal position to break open an ampoule received within the housing.

In another embodiment, the opening device further includes the housing forming a recessed guide channel for the push-rod, the push-rod being at least partially received within the recessed guide channel. The opening device may include a ball which is free rolling relative to the push-rod, and optionally which is at least partially received within a recessed guide channel. In other embodiments, the device includes a tether connecting the ball to the push-rod, and optionally the tethered ball is at least partially received within the recessed guide channel. The opening device may also include a ball including a pointed element positioned to contact an ampoule received within the housing when the ball is in the distal position.

In still further embodiments, the opening device includes a second push-rod received within the housing within a clearance space between the housing and an ampoule received therein, the second push-rod being axially movable in the distal direction from a proximal position in which a second ampoule received within the housing is intact, to a distal position in which the second ampoule received within the housing has been opened, the push button being attached to the second push-rod and being depressible distally relative to the housing and thereby moving the second push-rod from the proximal position to the distal position; and further includes a second ball adapted to be moved axially by axial movement of the second push-rod from the proximal position to the distal position, the second ball having a proximal position in which the second push-rod is in its proximal position and in which the second ampoule received within the housing remains intact, the second ball having a distal position in which the second push-rod is in its distal position and in which the second ampoule received within the housing is broken open, the housing defining a second distal guide portion which is ramped inwardly toward the second ampoule received in the housing, the second guide portion being configured to force the second ball to move inwardly as it moves axially from the proximal position to the distal position to break open the second ampoule received within the housing.

The opening device having a housing for receiving a second ampoule may also include the first and second push-rods and balls being configured to stagger the timing at which the first and second ampoules received within the housing are broken open. The dual-ampoule opening device may further include having the first and second balls free rolling relative to the first and second push-rods, or alternatively having the first and second balls are tethered to the first and second push-rods. In another dual-ampoule embodiment, one of the first and second balls is tethered to its respective push-rod and the other is free rolling relative to its respective push-rod.

Further embodiments include systems for delivering the content of a frangible ampoule comprising an opening device as disclosed herein containing a frangible ampoule received therein. Method embodiments for delivering the content of a frangible ampoule comprise placing a frangible ampoule within an opening device as described herein, and pressing the push button axially to move the push-rod and ball from the proximal position to the distal position.

What is claimed is:

1. An opening device for opening frangible ampoules comprising:
   a housing adapted to receive a frangible ampoule and having a proximal end and a distal end;
   a push-rod received within the housing within a clearance space between the housing and an ampoule received therein, the push-rod being axially movable in the distal direction from a proximal position in which an ampoule received within the housing is intact, to a distal position in which an ampoule received within the housing has been opened;
   a push button attached to the push-rod and having a portion exposed outside of the proximal end of the housing for contact by a user of the opening device, the push button being depressible distally relative to the housing and thereby moving the push-rod from the proximal position to the distal position; and
   a ball adapted to be moved axially by axial movement of the push-rod from the proximal position to the distal position, the ball having a proximal position in which the push-rod is in its proximal position and in which an ampoule received within the housing remains intact, the ball having a distal position in which the push-rod is in its distal position and in which an ampoule received within the housing is broken open, the ball being free rolling relative to the push-rod,
   the housing defining a distal guide portion which is ramped inwardly toward an ampoule received in the housing, the guide portion being configured to force the ball to move inwardly as it moves axially from the proximal position to the distal position to break open an ampoule received within the housing.

2. The opening device of claim 1 in which the housing forms a recessed guide channel for the push-rod, the push-rod being at least partially received within the recessed guide channel.

3. The opening device of claim 1 in which the hail is at least partially received within the recessed guide channel.

4. The opening device of claim 1 and further including a tether connecting the ball to the push-rod.

5. The opening device of claim 4 in which the housing forms a recessed guide channel for the push-rod, the push-rod being at least partially received within the recessed guide channel.

6. The opening device of claim 5 in which the ball is at least partially received within the recessed guide channel.

7. The opening device of claim 4 in which the ball includes a pointed element positioned to contact an ampoule received within the housing when the ball is in the distal position.

8. The opening device of claim 1 and which further includes a second push-rod received within the housing within a clearance space between the housing and an ampoule received therein, the second push-rod being axially movable in the distal direction from a proximal position in which a second ampoule received within the housing is intact, to a distal position in which the second ampoule received within the housing has been opened;
   the push button being attached to the second push-rod and being depressible distally relative to the housing and thereby moving the second push-rod from the proximal position to the distal position; and
   a second ball adapted to be moved axially by axial movement of the second push-rod from the proximal position to the distal position, the second ball having a proximal position in which the second push-rod is in its proximal position and in which the second ampoule received within the housing remains intact, the second ball having a distal position in which the second push-rod is in its distal position and in which the second ampoule received within the housing is broken open; and
   the housing defining a second distal guide portion which is ramped inwardly toward the second ampoule received in the housing, the second guide portion being configured to force the second ball to move inwardly as it moves axially from the proximal position to the distal position to break open the second ampoule received within the housing.

9. The opening device of claim 8 in which the first and second push-rods and balls are configured to stagger the timing at which first and second ampoules received within the housing are broken open.

10. The opening device of claim 8 in which both of the first and second balls are free rolling relative to the first and second push-rods, respectively.

11. The opening device of claim 8 in which both of the first and second balls are tethered to the first and second push-rods, respectively.

12. The opening device of claim 8 in which one of the first and second balls is tethered to its respective push-rod and the other is free rolling relative to its respective push-rod.

13. A system for delivering the content of a frangible ampoule comprising the opening device of claim 1 and a frangible ampoule received therein.

14. A method for delivery the content of a frangible ampoule comprising:
   placing a frangible ampoule with an opening device according to claim 1; and
   pressing the push button axially to move the push-rod and ball from the proximal position to the distal position.

* * * * *